US009266793B2

(12) United States Patent
Gee

(10) Patent No.: US 9,266,793 B2
(45) Date of Patent: Feb. 23, 2016

(54) ACID-CATALYZED OLEFIN OLIGOMERIZATIONS

(71) Applicant: Chevron Phillips Chemical Company LP, The Woodlands, TX (US)

(72) Inventor: Jeffery C. Gee, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 504 days.

(21) Appl. No.: 13/726,691

(22) Filed: Dec. 26, 2012

(65) Prior Publication Data

US 2014/0179964 A1 Jun. 26, 2014

(51) Int. Cl.
*C07C 2/08* (2006.01)
*C07C 2/28* (2006.01)
*C07C 2/14* (2006.01)
*C07C 2/16* (2006.01)
*C07C 5/25* (2006.01)
*C10G 50/00* (2006.01)

(52) U.S. Cl.
CPC ... *C07C 2/28* (2013.01); *C07C 5/25* (2013.01); *C10G 50/00* (2013.01); *C07C 2531/08* (2013.01); *C07C 2531/10* (2013.01); *C10G 2400/04* (2013.01)

(58) Field of Classification Search
CPC .................................. C07C 2/08; C07C 2/28
USPC ..................... 585/18, 329, 520, 526
See application file for complete search history.

(56) References Cited

U.S. PATENT DOCUMENTS

| 3,510,539 | A | * | 5/1970 | Fernald et al. ................. 585/522 |
| 3,940,452 | A | | 2/1976 | Strassberger |
| 3,957,664 | A | | 5/1976 | Heilman et al. |
| 4,029,601 | A | | 6/1977 | Wiese |
| 4,150,062 | A | | 4/1979 | Garwood et al. |
| 4,172,855 | A | | 10/1979 | Shubkin et al. |
| 4,367,352 | A | * | 1/1983 | Watts et al. ................... 585/254 |
| 4,469,912 | A | | 9/1984 | Blewett et al. |
| 4,531,014 | A | | 7/1985 | Gregory et al. |
| 4,547,613 | A | | 10/1985 | Garwood et al. |
| 4,658,078 | A | | 4/1987 | Slaugh et al. |
| 4,697,040 | A | | 9/1987 | Williamson et al. |
| 4,870,038 | A | | 9/1989 | Page et al. |
| 4,973,788 | A | | 11/1990 | Lin et al. |
| 5,053,569 | A | | 10/1991 | Marquis et al. |
| 5,087,788 | A | | 2/1992 | Wu |

(Continued)

FOREIGN PATENT DOCUMENTS

| CA | 1 034 967 | 7/1978 |
| FR | 2 302 289 | 9/1976 |

(Continued)

OTHER PUBLICATIONS

International Search Report and Written Opinion of the International Search Authority in International Application No. PCT/US2014/022636 dated May 16, 2014, 8 pages, (87woul).

(Continued)

*Primary Examiner* — In Suk Bullock
*Assistant Examiner* — Youngsul Jeong
(74) *Attorney, Agent, or Firm* — Merchant & Gould P.C.

(57) ABSTRACT

The present invention discloses processes for oligomerizing a monomer containing internal olefins using a solid acid catalyst. Illustrative monomers can contain at least 50 wt. % $C_6$ to $C_{24}$ internal olefins.

24 Claims, 10 Drawing Sheets

(56) References Cited

U.S. PATENT DOCUMENTS

| | | | |
|---|---|---|---|
| 5,191,130 | A | 3/1993 | Sanderson et al. |
| 5,284,988 | A * | 2/1994 | Schaerl et al. ............... 585/525 |
| 5,292,443 | A | 3/1994 | Esche, Jr. et al. |
| 5,498,815 | A | 3/1996 | Schaerfl, Jr. et al. |
| 6,407,302 | B1 | 6/2002 | Twu et al. |
| 6,548,723 | B2 | 4/2003 | Bagheri et al. |
| 6,639,118 | B1 | 10/2003 | McKinnie et al. |
| 6,680,417 | B2 | 1/2004 | Bagheri et al. |
| 7,078,579 | B2 | 7/2006 | Doll et al. |
| 7,273,957 | B2 | 9/2007 | Bakshi et al. |
| 7,332,637 | B2 | 2/2008 | Gee et al. |
| 7,989,670 | B2 | 8/2011 | Wu et al. |
| 8,067,652 | B2 | 11/2011 | Bburton et al. |
| 8,207,390 | B2 | 6/2012 | Wu et al. |
| 8,536,391 | B2 | 9/2013 | Small et al. |
| 2008/0146469 | A1 | 6/2008 | Sato et al. |
| 2009/0240012 | A1 | 9/2009 | Patil et al. |
| 2010/0317904 | A1 | 12/2010 | Small |
| 2011/0082323 | A1 | 4/2011 | Small et al. |
| 2015/0099679 | A1 | 4/2015 | Yang et al. |

FOREIGN PATENT DOCUMENTS

| | | |
|---|---|---|
| JP | 2008/143958 | 6/2008 |
| WO | WO 2009/073135 | 6/2009 |
| WO | WO 2009/117110 | 9/2009 |
| WO | WO 2013/055483 | 4/2013 |

OTHER PUBLICATIONS

Kissin et al, entitled "Post-Oligomerization of α-Olefin Oligomers: A Route to Single-Component and Multicomponent Synthetic Lubricating Oils," published in the *Journal of Applied Polymer Science*, vol. 111, (2009), pp. 273-280.

Honkela et al, entitled "Comparison of Ion-Exchange Resin Catalysts in the Dimerisation of Isobutene," published by Elsevier B.V., *Applied Catalysis A: General* 295 (2005), pp. 216-223.

Honkela et al., entitled "Kinetic Modeling of the Dimerization of Isobutene," published by American Chemical Society, *Ind. Eng. Chem. Res*. 2004, vol. 43, pp. 3251-3260.

DiGirolamo et al, entitled "Liquid-Phase Etherification/Dimerization of Isobutene over Sulfonic Acid Resins," published by American Chemical Society, *Ind. Eng. Chem. Res.* 1997, vol. 36, pp. 4452-4458.

Cruz et al, entitled "Conversion, Selectivity and Kinetics of the Liquid-Phase Dimerisation of Isoamylenes in the Presence of $C_1$ to $C_5$ Alcohols Catalysed by a Macroporous Ion-Exchange Resin," published by Elsevier Inc., *Journal of Catalysis* 238 (2006), pp. 330-341.

Shah, et al, entitled "Dimerization of Isoamylene: Ion Exchange Resin and Acid-Treated Clay as Catalysts," published by Elsevier Science Publishers B.V., Amsterdam, *Reactive Polymers*, vol. 19 (1993), pp. 181-190.

Shah, et al, entitled "Cross-Dimerization of α-Methylstyrene with Isoamylene and Aldol Condensation of Cyclohexanone Using a Cation-Exchange Resin and Acid-Treated Clay Catalysts," published by Elsevier Science B.V., Amsterdam, *Reactive Polymers*, vol. 22 (1994), pp. 19-34.

Cruz, et al, entitled "Kinetic Modelling of the Liquid-Phase Dimerization of Isoamylenes on Amberlyst 35," published by Elsevier Ltd., *Reactive & Functional Polymers*, vol. 67 (2007), pp. 210-224.

Haag, W.O. entitled "Oligomerization of Isobutylene on Cation Exchange Resins," published by *Chemical Engineering Progress, Symposium Series*, No. 73, vol. 63, (1967), pp. 140-146.

Schwarzer, et al, entitled "Kinetic Model for the Dimerisation of 1-Hexene Over a Solid Phosphoric Acid Catalyst," published by Elsevier B.V., *Applied Catalysis A: General* 340 (2008), pp. 119-124.

O'Connor et al, entitled "Alkene Oligomerization," published by 1990 Elsevier Science Publishers B.V., pp. 329-349.

Nierlich et al, entitled "Symposium on Alkylation, Aromatization, Oligomerization and Isomerization of Short Chain Hydrocarbons over Heterogeneous Catalysts," Presented before the Division of Petroleum Chemistry, Inc. American Chemical Society, New York City Meeting, Aug. 25-30, 1991, pp. 585-595.

Henry Z. Friedlander, *American Machine & Foundry Company, Springdale, Connecticut*, entitled "Organized Polymerization. I. Olefins on a Clay Surface," (1963) published by Journal of Polymer Science: Part C, No. 4, pp. 1291-1301.

De Klerk, et al, entitled "Butene Oligomerization by Phosphoric Acid Catalysis: Separating the Effects of Temperature and Catalyst Hydration on Product Selectivity," published by American Chemical Society, *Ind. Eng. Chem. Res*. 2006, vol. 45, pp. 6127-6136.

Adams, J. M. entitled "Synthetic Organic Chemistry Using Pillared, Cation-Exchanged and Acid-Treated Montmorillonite Catalysts—A Review," published by Elsevier Science Publishers B.V., *Applied Clay Science*, vol. 2, (1987), pp. 309-342.

Chiche, et al, entitled "Butene Oligomerization Over Mesoporous MTS-Type Aluminosilicates," published by Elsevier Science B.V., *Journal of Molecular Catalysis A: Chemical* 134 (1998), pp. 145-157.

Yoon, et al, entitled "Trimerization of Isobutene Over Cation Exchange Resins: Effect of Physical Properties of the Resins and Reaction Conditions," published by Elsevier B.V., *Journal of Molecular Catalysis A: Chemical* 260 (2006), pp. 181-186.

Kresnawahjuesa, et al, entitled "An Examination of Brønsted Acid Sites in H-[Fe]ZSM-5 for Olefin Oligomerization and Adsorption," published by Elsevier Science (USA), *Journal of Catalysis*, 2002, vol. 210, pp. 106-115.

Pater, et al. entitled "Oligomerization of Hex-1-ene Over Acidic Aluminosilicate Zeolites, MCM-41, and Silica-Alumina Co-gel Catalysts: A Comparative Study," published by Academic Press, Inc., *Journal of Catalysis*, vol. 184 (1999), pp. 262-267.

Sun et al, entitled "Dimerization of α-Methylstyrene (AMS) Catalyzed by Sulfonic Acid Resins: A Quantitative Kinetic Study," published by Academic Press, Inc., *Journal of Catalysis*, vol. 164, (1996), pp. 62-69.

Chaudhuri et al, entitled "Some Novel Aspects of the Dimerization of α-Methylstyrene with Acidic Ion-Exchange Resins, Clays, and Other Acidic Materials as Catalysts," published by American Chemical Society, *Ind. Eng. Chem. Res*. 1989, vol. 28, pp. 1757-1763.

Dixit et al, entitled "Deactivation of Ion-Exchange Resin Catalysts. Part II: Simulation by Network Models," published by Elsevier Science B.V., *Reactive & Functional Polymers*, vol. 31, (1996), pp. 251-263.

Kazansky, V.B. entitled "Solvation as a Main Factor that Determines the Strength of Liquid Superacids and the Selectivity of the Acid-Catalyzed Reactions of Olefins," published by Elsevier Science B.V., *Catalysis Today*, vol. 73 (2002), pp. 127-137.

Heveling et al, entitled "Chain-Length Distributions Obtained Over Nickel(II)-Exchanged or Impregnated Silica—Alumina Catalysts for the Oligomerization of Lower Alkenes," published by Springer Science+Business Media, Inc., *Catalysis Letters*, vol. 107, Nos. 1-2, Feb. 2006, pp. 117-121.

Hauge, et al, entitled "Oligomerization of Isobutene Over Solid Acid Catalysts," published by Elsevier B.V., *Catalysis Today*, vol. 100 (2005), pp. 463-466.

Gu et al, entitled "$SO_3H$—Functionalized Ionic Liquid as Efficient, Green and Reusable Acidic Catalyst System for Oligomerization of Olefins," published by Elsevier B.V., *Catalysis Communications*, vol. 4 (2003), pp. 597-601.

Coetzee, et al, entitled "An Improved Solid Phosphoric Acid Catalyst for Alkene Oligomerization in a Fischer—Tropsch Refinery," published by Elsevier B.V., *Applied Catalysis A: General* 308 (2006), pp. 204-209.

Schmidt et al, entitled "Oligomerization of $C_5$ Olefins in Light Catalytic Naphtha," published by American Chemical Society, *Energy & Fuels* 2008, vol. 22, pp. 1148-1155.

"AMBERLYST™ 15DRY Industrial Grade Strongly Acidic Catalyst," (Aug. 2005); © Rohm and Haas, 2006; 2 pgs.

"AMBERLYST™ 15WET Industrial Grade Strongly Acidic Catalyst for Catalysis and Separation technologies," (Nov. 2003); © Rohm and Haas, 2006; 4 pgs.

"AMBERLYST™ Polymeric Catalysts," *Dow, Water & Process Solutions*, (May 2011); 4 pgs.

SUPELCO Solutions within.™, entitled "Resins & Media," catalog published by *Sigma-Aldrich*, sigma-aldrich.com/analytical; pp. 1-50.

* cited by examiner

ACID-CATALYZED OLEFIN OLIGOMERIZATIONS

BACKGROUND OF THE INVENTION

The present invention relates generally to processes for oligomerizing olefins using a solid acid catalyst. In certain oligomerization processes, the solid acid catalyst can experience rapid catalyst deactivation, leading to relatively short catalyst lifetimes. It would be beneficial to develop oligomerization processes where catalyst lifetimes prior to deactivation are significantly improved. Accordingly, it is to this end that the present invention is directed.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

Processes for oligomerizing olefins in the presence of a solid acid catalyst are disclosed herein. In accordance with an embodiment of the present invention, one such process can comprise (i) contacting a monomer with a solid acid catalyst, and (ii) oligomerizing the monomer to form an oligomer product. In this process, the monomer can comprise at least 50 wt. % internal olefins.

In another embodiment disclosed herein, a process for forming an oligomer product can comprise (a) isomerizing an olefin feed comprising olefins to produce an internal olefin composition comprising internal olefins, (b) contacting the internal olefin composition comprising internal olefins with a solid acid catalyst, and (c) oligomerizing the olefins of the internal olefin composition to form the oligomer product. In this process, the olefins of the olefin feed can comprise at least 50 wt. % alpha olefins, and the olefins of the internal olefin composition comprising internal olefins can comprise at least 50 wt. % internal olefins. In some embodiments, the alpha olefins can be normal alpha olefins, and the internal olefins can be hydrocarbon internal olefins.

These processes can provide unexpectedly low catalyst deactivation rates and long catalyst lifetimes, which can result in stable olefin conversion and selectivity to various oligomers (e.g., dimers).

Both the foregoing summary and the following detailed description provide examples and are explanatory only. Accordingly, the foregoing summary and the following detailed description should not be considered to be restrictive. Further, features or variations can be provided in addition to those set forth herein. For example, certain embodiments can be directed to various feature combinations and sub-combinations described in the detailed description.

DEFINITIONS

Figure 1:
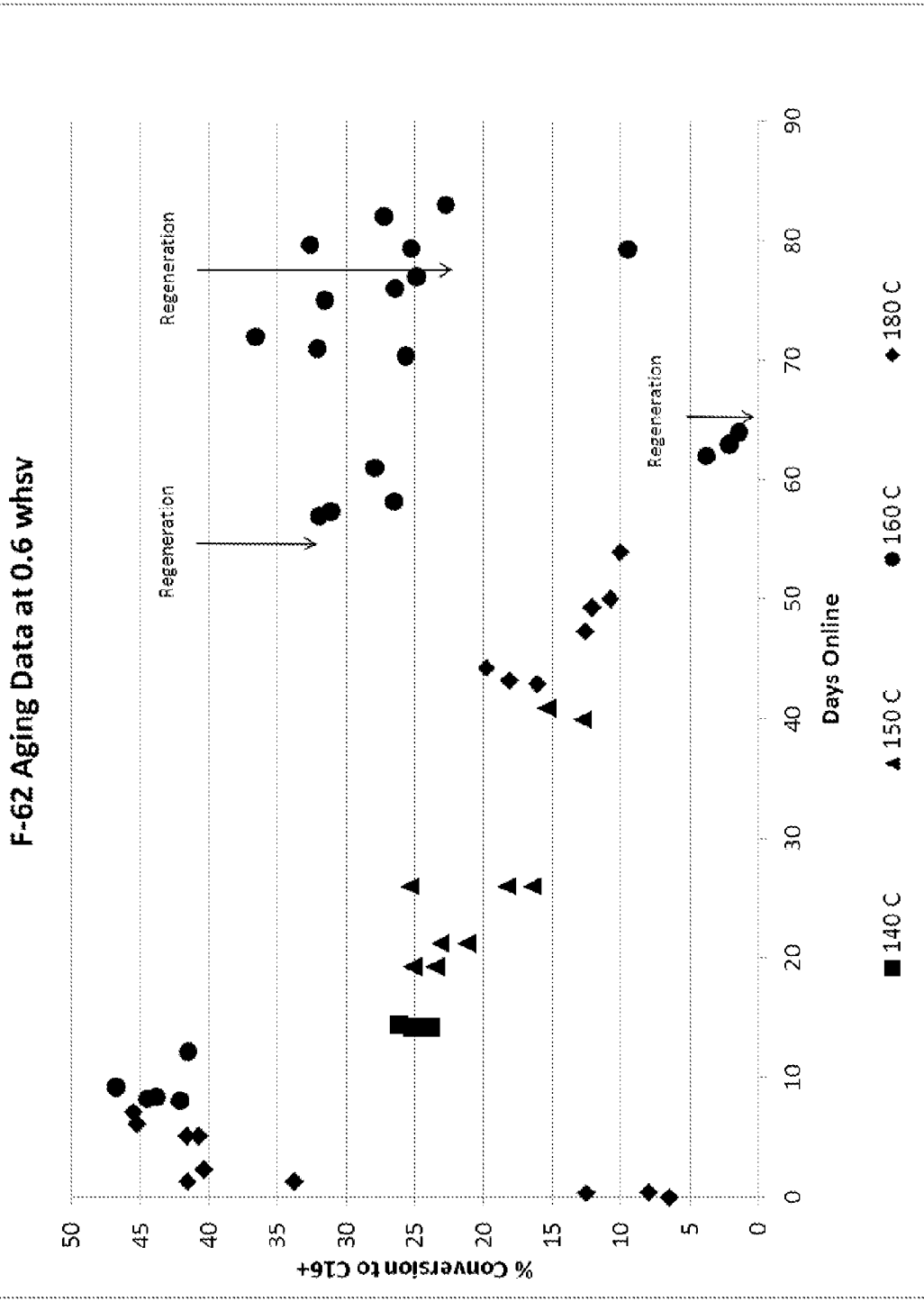
FIG. 1 presents a plot of the percentage conversion of 1-octene to $C_{16}+$ oligomer product as a function of time using Fitrol F-62 at 0.6 WHSV in Example 1.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a catalyst consisting of specific components; alternatively, consisting essentially of specific components; or alternatively, comprising the specific components and other non-recited components. While compositions and methods are described in terms of "comprising" various components or steps, the compositions and methods can also "consist essentially of" or "consist of" the various components or steps, unless specifically stated otherwise. For example, a monomer consistent with certain embodiments of the present invention can comprise; alternatively, consist essentially of; or alternatively, consist of; $C_6$ to $C_{24}$ internal olefins.

The terms "a," "an," and "the" are intended to include plural alternatives, e.g., at least one, unless otherwise specified. For instance, the disclosure of "a solid acid catalyst" is meant to encompass one, or mixtures or combinations of more than one, solid acid catalyst, unless otherwise specified.

For any particular compound or group disclosed herein, any name or structure presented is intended to encompass all conformational isomers, regioisomers, and stereoisomers that can arise from a particular set of substituents, unless otherwise specified. For example, a general reference to pentane includes n-pentane, 2-methyl-butane, and 2,2-dimethyl-propane, and a general reference to a butyl group includes an n-butyl group, a sec-butyl group, an iso-butyl group, and a t-butyl group. The name or structure also encompasses all enantiomers, diastereomers, and other optical isomers whether in enantiomeric or racemic forms, as well as mixtures of stereoisomers, as would be recognized by a skilled artisan, unless otherwise specified.

A chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogen atoms, as necessary for the situation, removed from an alkane. The disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

An aliphatic compound is an acyclic or cyclic, saturated or unsaturated compound, excluding aromatic compounds. An "aliphatic group" is a generalized group formed by removing one or more hydrogen atoms (as necessary for the particular group) from a carbon atom of an aliphatic compound. Aliphatic compounds, and therefore aliphatic groups, can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). While arene compounds and heteroarene compounds are mutually exclusive members of the group of aromatic compounds, a compound that has both an arene group and a heteroarene group is generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen-diphenyl ether; nitrogen-triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

The term "olefin" as used herein refers to compound that has at least one carbon-carbon double bond that is not part of an aromatic ring or ring system. The term "olefin" includes aliphatic, aromatic, cyclic or acyclic, and/or linear and branched compounds having at least one carbon-carbon double bond that is not part of an aromatic ring or ring system, unless specifically stated otherwise. The term "olefin," by itself, does not indicate the presence or absence of halogen atoms and/or the presence or absence of other carbon-carbon double bonds unless explicitly indicated. The terms "hydrocarbon olefin" or "olefin hydrocarbon" refer to olefin compounds containing only hydrogen and carbon, e.g., no halogens are present. Heteroatoms such as oxygen, nitrogen, sulfur, phosphorus, and the like, are not present in the olefin. Olefins can also be further identified by the position of the carbon-carbon double bond. It is noted that alkenes, alkamonoenes, alkadienes, alkatrienes, cycloalkenes, cycloalkamonoenes, cycloalkadienes, are members of the class of olefins.

The term "alpha olefin" as used herein refers to an olefin that has a double bond between the first and second carbon atom of a contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of halogens and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon, e.g., no halogens are present. Heteroatoms such as oxygen, nitrogen, sulfur, phosphorus, and the like, are not present in the alpha olefin.

The term "normal alpha olefin" as used herein refers to a linear hydrocarbon mono-olefin having a double bond between the first and second carbon atom.

The term "oligomerization," and its derivatives, refers to processes which produce a mixture of products containing at least 70 weight percent products containing from 2 to 60 olefin monomer units. An "oligomer" is a molecule that contains from 2 to 60 olefin monomer units (per molecule) and an "oligomerization product" or "oligomer product" includes all products made by the "oligomerization" process, including the "oligomers" and products which are not "oligomers" (e.g., products which contain more than 60 monomer units) and excludes non-oligomerized olefin monomer. It should be noted that the monomer units in the "oligomer" or "oligomerization product" do not have to be the same. For example, these terms are also used generically herein to include olefin homo-oligomers, co-oligomers, and so forth, and thus encompass products derived from any number of different olefin monomers disclosed herein. In like manner, oligomerizing (or oligomerization) is meant to encompasses dimerizing (or dimerization), trimerizing (or trimerization), and so forth.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another. Similarly, the term "contacting" is used herein to refer to materials which can be blended, mixed, slurried, dissolved, reacted, treated, or otherwise contacted in some other manner.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants can be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants can be unaware of at the time of the filing of the application.

DETAILED DESCRIPTION OF THE INVENTION

The present disclosure provides processes for oligomerizing olefins, in particular, for oligomerizing compositions containing internal olefins.

Oligomerization of Internal Olefins

Embodiments of this invention are directed to processes for forming an oligomer product. Such oligomerization processes can comprise (or consist essentially of, or consist of): (i) contacting a monomer with a solid acid catalyst; and (ii) oligomerizing the monomer to form an oligomer product. In an embodiment, the monomer can comprise at least 50 wt. % internal olefins.

Generally, the features of the processes (e.g., the components and/or features of the monomer, the olefins (e.g., carbon number and/or olefin type, among other olefin features) of the monomer, the solid acid catalyst, and the conditions under which the oligomer product is formed, among others) are independently described herein and these features can be combined in any combination to further describe the disclosed oligomerization processes.

In some embodiments, the monomer can comprise, consist essentially of, of consist of, $C_6$ to $C_{24}$ internal olefins. Moreover, the monomer can comprise, consist essentially of, or consist of, any single carbon number internal olefins from $C_6$ to $C_{24}$ (e.g., $C_8$ internal olefins) or any combination of different single carbon number internal olefins from $C_6$ to $C_{24}$ (e.g., $C_8$ to $C_{16}$ internal olefins, or $C_8$, $C_{12}$, and $C_{16}$ internal olefins, among other combinations). Monomers, olefins, and internal olefins are described herein and their features can be utilized without limitation to further describe the monomer, olefins, and/or internal olefins which can be utilized in the oligomerization processes. In some embodiments, an oligomerization process can utilize a single solid acid catalyst; or alternatively, the process can utilize more than one solid acid catalyst. Solid acid catalysts are described herein and these acid catalysts can be utilized without limitation in the oligomerization processes.

In some embodiments, the contacting step can include contacting the monomer comprising olefins, the solid acid catalyst, and additional unrecited materials (e.g., a non-olefin solvent or diluent, a stabilizer, amongst other materials). In other embodiments, the contacting step can consist essentially of contacting the monomer comprising olefins and the solid acid catalyst or, alternatively, consist of contacting the monomer comprising olefins and the solid acid catalyst. Likewise, additional materials or features can be employed in the oligomerizing step. For instance, the formation of the oligomer product can occur in the presence of a non-olefin solvent. The amount of any non-olefin solvent used in addition to the disclosed internal olefins in the contacting step and/or the oligomerizing step of the process is not limited to any particular range. Such solvent, or combination of solvents, can be used, for example, as a flow modifier to alter the flow properties or viscosity of the monomer (or olefins) and/or the flow properties of the oligomer product. Non-olefin solvents which can be utilized are described herein, and these solvents can be utilized without limitation in the oligomerization processes described herein.

Independently, the contacting step and the oligomerizing step of the process for forming an oligomer product can be conducted at a variety of temperatures, pressures, and time periods. For instance, the temperature at which the monomer and the solid acid catalyst are initially contacted can be the same as, or different from, the temperature at which the oligomer product is formed. As an illustrative example, in the contacting step, the monomer and the solid acid catalyst can be contacted initially at temperature T1 and, after this initial combining, the temperature can be changed to a temperature T2 to allow for the oligomerizing of the monomer to form the oligomer product. Likewise, the pressure can be different in the contacting step than in the oligomerizing step. Often, the time period in the contacting step can be referred to as the contact time, while the time period in the oligomerizing step can be referred to as the reaction time. The contact time and the reaction time can be, and often are, different.

In an embodiment, the contacting step and/or the oligomerizing step of the process for forming an oligomer product can be conducted at any temperature below a maximum operating temperature of the solid acid catalyst (e.g., any temperature at which the solid acid catalyst is thermally stable), for example, 5° C., 10° C., 15° C., or 20° C. less than the maximum operating temperature of the solid acid catalyst. For instance, the contacting step and/or the oligomerizing step can be conducted at a minimum temperature of 50° C., 60° C., 65° C., or 70° C.; or alternatively, at a maximum temperature of 140° C., 130° C., 125° C., 120° C., 120° C., 115° C., or 110° C. In an embodiment, the contacting step and/or the oligomerizing step can be conducted at a temperature in a range from any minimum temperature disclosed herein to any maximum temperature disclosed herein. In some non-limiting embodiments, the contacting step and/or the oligomerizing step can be conducted at temperature in a range from 50° C. to 140° C.; alternatively, from 70° C. to 140° C.; alternatively, from 50° C. to 125° C.; alternatively, from 60° C. to 130° C.; alternatively, from 65° C. to 120° C.; alternatively, from 70° C. to 125° C.; or alternatively, from 70° C. to 120° C. In other non-limiting embodiments, the contacting step and/or the oligomerizing step can be conducted at a temperature in a range from 75° C. to 115° C., from 80° C. to 115° C., from 80° C. to 110° C., or from 85° C. to 110° C. Other temperature ranges for the contacting step and/or the oligomerizing step are readily apparent from this disclosure. These temperature ranges also are meant to encompass circumstances where either the contacting step, the oligomerizing step, or both, can be conducted at a series of different temperatures, instead of at a single fixed temperature, falling within the respective temperature ranges.

While not being limited thereto, the contacting step and/or the oligomerizing step of the process for forming an oligomer product can be conducted at a reactor pressure in a range from 5 to 150 psig, or alternatively, from 10 to 100 psig. In some embodiments, the contacting step and/or the oligomerizing step can be conducted at atmospheric pressure, while in other embodiments, the contacting step and/or the oligomerizing step can be conducted at sub-atmospheric pressures.

Often, the process for forming an oligomer product can be a flow process and/or a continuous process. In such circumstances, the monomer-solid acid catalyst contact time (or reaction time) can be expressed in terms of weight hourly space velocity (WHSV)—the ratio of the weight of the monomer which comes in contact with a given weight of solid acid catalyst per unit time (units of g/g/hr). While not limited thereto, the WHSV employed for the process of producing an oligomer product can have a minimum value of 0.05, 0.1, 0.25, 0.5, 0.75, or 1; or alternatively, a maximum value of 5, 4, 3, 2.5, or 2. In an embodiment, the WHSV can be in a range from any minimum WHSV disclosed herein to any maximum WHSV disclosed herein. In a non-limiting example, the WHSV can be in a range from 0.05 to 5; alternatively, from 0.05 to 4; alternatively, from 0.1 to 5; alternatively, from 0.1 to 4; alternatively, from 0.1 to 3; alternatively, from 0.1 to 2; alternatively, from 0.1 to 1; alternatively, from 0.1 to 0.8; alternatively, from 0.5 to 5; alternatively, from 0.5 to 4; alternatively, from 0.5 to 3; alternatively, from 0.8 to 3; or alternatively, from 1 to 3. Other WHSV ranges are readily apparent from this disclosure. Any suitable reactor or vessel can be used to form the oligomer product, non-limiting examples of which can include a flow reactor, a continuous reactor, a packed tube, and a stirred tank reactor, including more than one reactor in series or in parallel, and including any combination of reactor types and arrangements.

In an embodiment, the minimum monomer conversion can be at least 10%, by weight percent or by mole percent. The conversion of the monomer is described as "monomer conversion" to indicate that the percentage conversion, in weight percent or in mole percent, is based on the monomer and does not include non-monomer materials that can be present. In another embodiment, the minimum monomer conversion can be at least 15%, at least 20%, at least 25%, at least 30%, at least 40%, or at least 50%, and these percentages can be weight percentages or mole percentages. In yet another embodiment, the maximum monomer conversion can be 90%, 85%, 80%, 75%, 70%, 65%, 60%, or 55%, and these percentages can be weight percentages or mole percentages. Generally, the monomer conversion can be in a range from any minimum monomer conversion disclosed herein to any maximum monomer conversion disclosed herein. Non-limiting ranges of monomer conversion, in weight or mole percentages, can include, but are not limited to, the following ranges: from 10% to 90%, from 10% to 85%, from 10% to 75%, from 15% to 90%, from 15% to 75%, from 10% to 60%, from 10% to 50%, from 15% to 50%, from 10% to 45%, from 15% to 45%, from 10% to 40%, or from 15% to 45%. Other monomer conversion ranges are readily apparent from this disclosure. In some embodiments, these monomer conversions can be achieved in a batch process, while in other embodiments, these monomer conversions can be achieved in a flow or continuous process, such as, for example, a single pass thru a reactor (e.g., a fixed bed reactor).

In another embodiment, the minimum internal olefin conversion can be at least 10%, by weight percent or by mole percent. In this regard, the conversion of the internal olefin is described as "internal olefin conversion" to indicate that the percentage conversion, in weight percent or in mole percent, is based on the internal olefins of the monomer, and does not include non-internal olefins that can be present. In another embodiment, the minimum internal olefin conversion can be at least 15%, at least 20%, at least 25%, at least 30%, at least 40%, or at least 50%, and these percentages can be weight percentages or mole percentages. In yet another embodiment, the maximum internal olefin conversion can be 90%, 85%, 80%, 75%, 70%, 65%, 60%, or 55%, and these percentages can be weight percentages or mole percentages. Generally, the internal olefin conversion can be in a range from any minimum internal olefin conversion disclosed herein to any maximum internal olefin conversion disclosed herein. Non-limiting ranges of internal olefin conversion, in weight or mole percentages, can include, but are not limited to, the following ranges: from 10% to 90%, from 10% to 85%, from 10% to 75%, from 15% to 90%, from 15% to 75%, from 10% to 60%, from 10% to 50%, from 15% to 50%, from 10% to 45%, from 15% to 45%, from 10% to 40%, or from 15% to 45%. Other internal olefin conversion ranges are readily apparent from this disclosure. In some embodiments, these internal olefin conversions can be achieved in a batch process, while in other embodiments, these internal olefin conversions can be achieved in a flow or continuous process, such as, for example, a single pass thru a reactor (e.g., a fixed bed reactor).

In an embodiment, the processes disclosed herein can be conducted for relatively long periods of time with low rates of catalyst deactivation (e.g., long catalyst lifetimes), and with relatively stable conversions over these time periods. For example, a monomer conversion (or internal olefin conversion, or single pass monomer conversion, or single pass internal olefin conversion) to the oligomer product can be maintained substantially constant for a minimum time period of at least 5 days. In this context, "substantially constant" means that the monomer conversion (or internal olefin conversion, or single pass monomer conversion, or single pass internal olefin conversion) is within a range of +/−25% range, as measured in weight percent or mole percent as the context requires. Thus, for example, if a single pass internal olefin conversion is substantially constant at 20 weight percent for a period of at least 5 days, the range of the single pass internal olefin conversion during this 5-day period can be between 15 and 25 wt. %. In some embodiments, the monomer conversion (or internal olefin conversion, or single pass monomer conversion, or single pass internal olefin conversion) to the oligomer product can be maintained substantially constant for a minimum time period of at least 7 days; alternatively, at least 10 days; alternatively, at least 14 days; alternatively, at least 21 days; or alternatively, at least 30 days. In other embodiments, the monomer conversion (or internal olefin conversion, or single pass monomer conversion, or single pass internal olefin conversion) to the oligomer product can be maintained substantially constant for a maximum time period of 75 days, 60 days, 45 days, or 30 days. Generally, the monomer conversion (or internal olefin conversion, or single pass monomer conversion, or single pass internal olefin conversion) to the oligomer product can be maintained substantially constant in a range from any minimum time period to any maximum time period disclosed herein. In some non-limiting embodiments, the monomer conversion (or internal olefin conversion, or single pass monomer conversion, or single pass internal olefin conversion) to oligomer product can be maintained substantially constant for a time period in a range from 5 to 60 days, from 7 to 60 days, from 10 to 60 days, from 5 to 45 days, from 7 to 45 days, from 10 to 45 days, from 5 to 30 days, from 7 to 30 days, or from 10 to 30 days. Other time periods are readily apparent from this disclosure. Moreover, these relatively stable monomer conversions (or internal olefin conversions, or single pass monomer conversions, or single pass internal olefin conversions) often can be maintained to within a range of +/−20%, within a range of +/−15%, or within a range of +/−10%, in certain embodiments, for these long periods of time. In some embodiments, these long periods of time with stable single pass conversions can be achieved in a flow or continuous process, such as, for example, a single pass thru a reactor (e.g., a fixed bed reactor).

Monomers Containing Olefins

Embodiments of this invention are directed to processes comprising contacting a monomer comprising internal olefins with a solid acid catalyst, and oligomerizing the monomer to form an oligomer product. A wide range of monomers comprising, consisting essentially of, or consisting of, internal olefins can be oligomerized according to the methods provided herein, and using the acid catalysts disclosed herein. In any embodiment wherein the monomer comprises internal olefins, the monomer can further comprise alpha olefins. Consequently, in some embodiments, the oligomerization processes disclosed herein can employ a monomer which is a mixture of internal olefins and alpha olefins. In some embodiments, the monomer (internal olefins and/or alpha olefins) can comprise a hydrocarbon olefin.

Generally, the monomer can comprise (or consist essentially of, or consist of) $C_4$ to $C_{24}$ olefins, or alternatively, $C_6$ to $C_{24}$ olefins. In one embodiment, the monomer can comprise (or consist essentially of, or consist of) $C_8$ to $C_{24}$ olefins, while in another embodiment, the monomer can comprise (or consist essentially of, or consist of) $C_8$ to $C_{22}$ olefins, or $C_8$ to $C_{20}$ olefins. In yet another embodiment, the monomer can comprise $C_8$ to $C_{16}$ olefins, $C_8$ to $C_{12}$ olefins, $C_8$ to $C_{10}$ olefins, $C_{12}$ to $C_{16}$ internal olefins, or $C_{14}$ to $C_{16}$ olefins. In other embodiments, the monomer can comprise (or consist essentially of, or consist of) $C_4$ olefins; alternatively, $C_6$ olefins; alternatively, $C_8$ olefins; alternatively, $C_{10}$ olefins; alternatively, $C_{12}$ olefins; alternatively, $C_{14}$ olefins; alternatively, $C_{16}$ olefins; or alternatively, $C_{18}$ olefins. Thus, mixtures of olefins having different numbers of carbon atoms can be used, or olefins having predominantly a single number of carbon atoms can be used as the monomer.

In an embodiment, the monomer can comprise at least 50 wt. %, at least 55 wt. %, at least 60 wt. %, at least 65 wt. %, at least 70 wt. %, at least 75 wt. %, at least 80 wt. %, at least 85 wt. %, at least 90 wt. %, at least 92.5 wt. %, or at least 95 wt. %, internal olefins of any carbon number range described herein; alternatively, of any combination of single carbon numbered internal olefins described herein; or alternatively, of any single carbon numbered internal olefins described herein. Moreover, in a particular embodiment contemplated herein, the monomer can comprise, consist essentially of, or consist of, hydrocarbon internal olefins.

In these and other embodiments, the internal olefins can be cyclic or acyclic, and/or linear or branched. For example, the monomer can comprise, consist essentially of, or consist of, cyclic internal olefins; additionally or alternatively, the monomer can comprise, consist essentially of, or consist of, linear internal olefins. Moreover, the monomer can comprise olefins having only one olefin moiety (mono-olefins) and/or olefins having two olefin moieties (di-olefins), as well as compounds having more than two olefin moieties per molecule; alternatively, mono-olefins; alternatively, di-olefins; or alternatively, olefins having more than two olefin moieties per molecule.

The monomer can comprise linear and/or branched internal olefins, and therefore, mixtures of linear and branched internal olefins can be used. Suitable branched internal olefins can, for example, have a branch at any position and can have the double bond at any non-primary position. In one embodiment, the branched internal olefin can have more than one branch. In another embodiment, the branched internal olefin can have one or more branches at the carbon-carbon double bond; or alternatively, the branched internal olefin can have one or more branches on carbon atoms that are not part of a carbon-carbon double bond. In yet another embodiment, the internal olefins can comprise, consist essentially of, or consist of, linear internal olefins.

Consistent with embodiments of this disclosure are processes which can comprise contacting a monomer comprising internal olefins with a solid acid catalyst, and oligomerizing the monomer to form an oligomer product, wherein the monomer can comprise at least 50 wt. % internal olefins. As described herein, the contacting step can include other non-recited components or materials, such as, for example, a non-olefin solvent. Accordingly, a non-olefin solvent, or other materials, can be present when the monomer and the solid acid catalyst are contacted at, for example, a solvent to monomer weight ratio of less than 10:1, less than 5:1, less than 3:1, less than 2:1, less than 1:1, less than 0.75:1, less than 0.5:1, less than 0.35:1, less than 0.25:1, less than 0.15:1, or less than 0.1:1.

Generally, the carbon number of the monomer, the types of internal olefins, and the weight percentage of internal olefins can be combined in any fashion to describe the internal olefins which can be utilized as the monomer. Additionally, the monomer can comprise other olefins other than internal olefins. For example, in some non-limiting embodiments, the monomer can comprise (or consist essentially of, or consist of) at least 50 wt. %, at least 60 wt. %, at least 70 wt. %, at least 80 wt. %, or at least 90 wt. %, of $C_6$ to $C_{24}$ hydrocarbon internal olefins; alternatively, $C_8$ to $C_{24}$ hydrocarbon internal olefins; alternatively, $C_8$ to $C_{20}$ hydrocarbon internal olefins; alternatively, $C_8$ to $C_{16}$ hydrocarbon internal olefins; alternatively, $C_6$ hydrocarbon internal olefins; alternatively, $C_8$ hydrocarbon internal olefins; alternatively, $C_{10}$ hydrocarbon internal olefins; alternatively, $C_{12}$ hydrocarbon internal olefins; alternatively, $C_{14}$ hydrocarbon internal olefins; alternatively, $C_{16}$ hydrocarbon internal olefins; or alternatively, $C_{18}$ hydrocarbon internal olefins. Other internal olefins which can be utilized are readily apparent from the present disclosure. Additionally, the monomer can comprise olefins other than internal olefins as described herein.

As described herein, the monomer can include alpha olefins. Alpha olefin carbon numbers and carbon number ranges are described herein and these carbon numbers and carbon number ranges can be utilized without limitation to further describe the alpha olefins which can be present in the monomer. In some embodiments, the monomer can comprise less than 15 wt. % alpha olefins, less than 10 wt. % alpha olefins, less than 9 wt. % alpha olefins, less than 8 wt. % alpha olefins, less than 7 wt. % alpha olefins, less than 6 wt. % alpha olefins, or less than 5 wt. % alpha olefins. In some embodiments, the monomer employed in the oligomerization processes disclosed herein can comprise less than 4 wt. % alpha olefins, less than 3 wt. % alpha olefins, or less than 2 wt. % alpha olefins. In some embodiments, the alpha olefins can be normal alpha olefins.

In an embodiment, the monomer disclosed herein can be further characterized as being substantially free of oxygen-containing compounds. The term "substantially free" in this context means that less than 100 ppm (by weight) of oxygen-containing compounds are present in the monomer prior to contacting the monomer with the solid acid catalyst. In another embodiment, the monomer can comprise less than 75 ppm; alternatively, less than 50 ppm; alternatively, less than 25 ppm; alternatively, less than 10 ppm; alternatively, less than 5 ppm; or alternatively, less than 3 ppm, of oxygen-containing compounds. Additionally, the quantities of oxygen-containing compounds disclosed herein for the monomer can be applied to any solvent or other material that can be optionally utilized in the oligomerization process. While not wishing to be bound by theory, Applicants believe that oxygen-containing compounds (e.g., molecular oxygen, water, peroxides, alcohols, ketones, etc.) can interact and/or bind with catalyst sites on the solid acid catalyst and adversely affect catalytic activity.

Likewise, in another embodiment, the monomer disclosed herein can be further characterized as being substantially free of nitrogen-containing compounds. The term "substantially free" in this context means that less than 100 ppm (by weight) of nitrogen-containing compounds are present in the monomer prior to contacting the monomer with the solid acid catalyst. In another embodiment, the monomer can comprise less than 75 ppm; alternatively, less than 50 ppm; alternatively, less than 25 ppm; alternatively, less than 10 ppm; alternatively, less than 5 ppm; or alternatively, less than 3 ppm, of nitrogen-containing compounds. Additionally, the quantities of nitrogen-containing compounds disclosed herein for the monomer can be applied to any solvent or other material that can be optionally utilized in the oligomerization process. While not wishing to be bound by theory, Applicants believe that nitrogen-containing compounds (e.g., amines, ammonia, etc.) can interact and/or bind with catalyst sites on the solid acid catalyst and adversely affect catalytic activity. In this disclosure, the term "nitrogen-containing compounds" does not include molecular nitrogen ($N_2$). In some embodiments, the oligomerization processes disclosed herein can be conducted in an inert gas (e.g., $N_2$, argon, helium, etc.) atmosphere.

Olefin Feeds

There are many possible sources for the monomer comprising internal olefins that can be employed in the processes described herein. For instance, internal olefins can be produced by isomerizing alpha olefins, one exemplary process of which is described in U.S. Pat. No. 7,332,637, the disclosure of which is incorporated herein by reference in its entirety. Internal olefins also can be prepared via a separation and/or distillation procedure. Additional suitable processes for preparing internal olefins are known to those of skill in the art.

Embodiments of this invention are directed to processes for forming an oligomer product, such as by contacting a monomer comprising internal olefins (e.g., $C_6$ to $C_{24}$ internal olefins, among other monomers disclosed herein) with a solid acid catalyst, and oligomerizing the monomer to form an oligomer product. Optionally, this process can further comprise a step of isomerizing an olefin feed to form internal olefins (which can be utilized as the monomer).

Accordingly, in certain embodiments, a process for forming an oligomer product (or a process for oligomerizing olefins) can comprise (a) isomerizing an olefin feed comprising olefins to form an internal olefin composition comprising internal olefins, (b) contacting the internal olefin composition comprising internal olefins with a solid acid catalyst, and (c) oligomerizing the olefins of the internal olefin composition comprising internal olefins to form the oligomer product. Optionally, this process can further comprise a step of removing residual alpha olefin from the internal olefin composition comprising internal olefins after isomerizing the olefin feed. In these processes, the olefins of the olefin feed can comprise at least 50 wt. % alpha olefins and the olefins of the internal olefin composition comprising internal olefins can comprise at least 50 wt. % internal olefins. In some embodiments, the alpha olefins are normal alpha olefins and the internal olefins are hydrocarbon internal olefins. Generally, the olefins in the internal olefin composition comprising internal olefins represent, and can have the same features (without limitation), as the monomer of the monomer oligomerization processes described herein. Generally, the features of the processes for forming an oligomer product (e.g., the components and/or features of the olefin feed comprising alpha olefins, the features of the alpha olefins, the components of the internal olefin composition, the features of the internal olefins, the amount of internal olefins in the internal olefin composition, the solid acid catalyst, and the conditions under which the oligomer product is formed, among others) are independently described herein and these features can be combined in any combination to further describe the disclosed processes for forming an oligomer product. The olefins of the olefin feed are described herein and any aspect or embodiment of the olefins can be utilized without limitation to describe the process for forming an oligomer product.

Generally, the olefins of the olefin feed can have the same carbon number(s), or carbon number ranges, as the monomer described herein for the oligomerization processes. In an embodiment, the olefins of the olefin feed can comprise, consist essentially of, or consist of, alpha olefins; alternatively, hydrocarbon alpha olefins; or alternatively, normal alpha olefins. In an embodiment, the olefins of the olefin feed can comprise at least 50 wt. %, at least 60 wt. %, at least 70 wt. %, at least 75 wt. %, at least 80 wt. %, at least 85 wt. %, at least 90 wt. %, at least 92.5 wt. %, or at least 95 wt. %, alpha olefins (or hydrocarbon alpha olefins, or normal alpha olefins). Generally, the carbon number of the olefins of the olefin feed, the type of olefins of the olefin feed, and the weight percentage of olefin type(s) for the olefins of the olefin feed can be combined in any fashion to describe the olefins of the olefin feed.

In a non-limiting embodiment, the olefins of the olefin feed can comprise at least 50 wt. % normal alpha olefins, at least 55 wt. % normal alpha olefins, at least 60 wt. % normal alpha olefins, at least 65 wt. % normal alpha olefins, at least 70 wt. % normal alpha olefins, or at least 75 wt. % normal alpha olefins. Moreover, the olefins of the olefin feed can comprise at least 80 wt. % normal alpha olefins, at least 85 wt. % normal alpha olefins, at least 90 wt. % normal alpha olefins, or at least 95 wt. % normal alpha olefins, in certain embodiments.

In a non-limiting embodiment, the olefins of the olefin feed can comprise (or consist essentially of, or consist of) $C_4$ to $C_{24}$ normal alpha olefins, and more often, $C_6$ to $C_{24}$ normal alpha olefins. In one embodiment, the olefins of the olefin feed can comprise $C_8$ to $C_{24}$ normal alpha olefins, while in another embodiment, the olefins of the olefin feed can comprise $C_8$ to $C_{22}$ normal alpha olefins, or $C_8$ to $C_{20}$ normal alpha olefins. In yet another embodiment, the olefins of the olefin feed can comprise $C_8$ to $C_{16}$ normal alpha olefins. In other embodiments, the olefins of the olefin feed can comprise (or consist essentially of, or consist of) 1-hexene, 1-octene, 1-decene, 1-dodecene, 1-tetradecene, 1-hexadecene, 1-octadecene, or any combination thereof; alternatively, 1-butene; alternatively, 1-hexene; alternatively, 1-octene; alternatively, 1-decene; alternatively, 1-dodecene; alternatively, 1-tetradecene; alternatively, 1-hexadecene; or alternatively, 1-octadecene. Thus, mixtures of various normal alpha olefins having different numbers of carbon atoms can be used, or normal alpha olefins having predominantly a single number of carbon atoms can be used. In some non-limiting embodiments, the olefin feed comprising normal alpha olefins can, in some embodiments, comprise at least 50 wt. %, at least 60 wt. %, at least 70 wt. %, at least 75 wt. %, at least 80 wt. %, at least 85 wt. %, at least 90 wt. %, at least 92.5 wt. %, or at least 95 wt. %, of any carbon number range of normal alpha olefins described herein; alternatively, of any combination of single carbon numbered normal alpha olefins described herein; or alternatively, of any single carbon numbered normal alpha olefin described herein.

For instance, in a non-limiting example, the olefins of the olefin feed can comprise at least 75 wt. %, at least 80 wt. %, at least 85 wt. %, at least 90 wt. %, or at least 95 wt. %, of 1-hexene; alternatively, 1-octene; alternatively, 1-decene; alternatively, 1-dodecene; alternatively, 1-tetradecene; alternatively, 1-hexadecene; or alternatively, 1-octadecene.

Generally, the features of the olefins of the olefin feed and the features of the olefins of the internal olefin composition are independent of each other and these features can be combined in any fashion to further describe the isomerization/oligomerization processes. In some non-limiting embodiments, the olefins of the olefin feed can comprise at least 75 wt. % $C_6$ to $C_{24}$ normal alpha olefins (or at least 80 wt. % $C_6$ to $C_{24}$ normal alpha olefins, or at least 85 wt. % $C_6$ to $C_{24}$ normal alpha olefins, or at least 90 wt. % $C_6$ to $C_{24}$ normal alpha olefins), and the olefins of the internal olefin composition can comprise (e.g., after isomerizing) less than 10 wt. % $C_6$ to $C_{24}$ normal alpha olefins (or less than 7 wt. % $C_6$ to $C_{24}$ normal alpha olefins, or less than 5 wt. % $C_6$ to $C_{24}$ normal alpha olefins, or less than 2 wt. % $C_6$ to $C_{24}$ normal alpha olefins).

Solid Acid Catalysts

In some embodiments, the catalyst employed in the oligomerization of a monomer comprising internal olefins, for example, $C_6$ to $C_{24}$ internal olefins, can be a solid acid catalyst. A single type of solid acid catalyst can be employed, or the oligomerization process can employ more than one type of solid acid catalyst.

In one embodiment, the solid acid catalyst can comprise (or consist essentially of, or consist of) an acidic ion exchange resin. In another embodiment, the solid acid catalyst can comprise (or consist essentially of, or consist of) a styrene-divinylbenzene polymer resin, a functionalized styrene-divinylbenzene polymer resin, a functionalized polymer resin comprising units derived from styrene and units derived from divinyl benzene, a 4-vinylpyridine divinylbenzene polymer resin, an ionomer resin, a tetrafluoroethylene polymer resin modified with perfluorovinyl ether groups terminated with sulfonate groups, or any combination thereof; or alternatively, a styrene-divinylbenzene polymer resin, a functionalized styrene-divinylbenzene polymer resin, a functionalized polymer resin comprising units derived from styrene and units derived from divinyl benzene, or any combination thereof. In yet another embodiment, the solid acid catalyst can comprise (or consist essentially of, or consist of) a styrene-divinylbenzene polymer resin; alternatively, a functionalized styrene-divinylbenzene polymer resin; alternatively, a functionalized polymer resin comprising units derived from styrene and units derived from divinyl benzene; alternatively, a 4-vinylpyridine divinylbenzene polymer resin; alternatively, an ionomer resin; or alternatively, a tetrafluoroethylene polymer resin modified with perfluorovinyl ether groups terminated with sulfonate groups.

Commercially available acidic resins that can be employed as the solid acid catalyst in embodiments disclosed herein can include AMBERLYST® resins, NAFION® resins, or any combination thereof. Thus, for example, the solid acid catalyst can comprise an AMBERLYST® resin; or alternatively, a NAFION® resin. Various grades of the AMBERLYST® resin and/or the NAFION® resin can be used as the solid acid catalyst. While not limited thereto, the solid acid catalyst can comprise (or consist essentially of, or consist of) AMBERLYST® 15 resin, AMBERLYST® 31 resin, AMBERLYST® 35 resin, AMBERLYST® 36 resin, AMBERLYST® DT resin, or any combination thereof; alternatively, AMBERLYST® 15 resin; alternatively, AMBERLYST® 31 resin; alternatively, AMBERLYST® 35 resin; alternatively, AMBERLYST® 36 resin; or alternatively, AMBERLYST® DT resin.

The solid acid catalyst can be modified or functionalized with an organic acid and/or an inorganic acid; alternatively, an organic acid; or alternatively, an inorganic acid. In some embodiments, the solid acid catalyst can be modified with a carboxylic acid, a sulfonic acid, or any combination thereof; alternatively, a carboxylic acid; or alternatively, a sulfonic acid. In an embodiment, the carboxylic acid can be a $C_1$ to $C_{20}$ carboxylic acid; alternatively, a $C_1$ to $C_{15}$ carboxylic acid; or alternatively, a $C_1$ to $C_{10}$ carboxylic acid. In an embodiment, the sulfonic acid can be a $C_1$ to $C_{20}$ sulfonic acid; alternatively, a $C_1$ to $C_{15}$ sulfonic acid; or alternatively, a $C_1$ to $C_{10}$ sulfonic acid. In a non-limiting embodiment, the acid which can be utilized to modify the solid acid catalyst can comprise, consist essentially of, or consist of, benzoic acid, formic acid, acetic acid, propionic acid, butyric acid, oxalic acid, trifluoroacetic acid, trichloroacetic acid, sulfamic acid, benzene sulfonic acid, toluene sulfonic acid (ortho, meta, and/or para), dodecylbenzene sulfonic acid, naphthalene sulfonic acid, dinonylnaphthalene disulfonic acid, methane sulfonic acid, or any combination thereof; alternatively, benzoic acid, formic acid, acetic acid, propionic acid, butyric acid, oxalic acid, trifluoroacetic acid, trichloroacetic acid, or any combination thereof; or alternatively, benzene sulfonic acid, toluene sulfonic acid (ortho, meta, and/or para), dodecylbenzene sulfonic acid, naphthalene sulfonic acid, dinonylnaphthalene disulfonic acid, methane sulfonic acid, or any combination thereof. In a non-limiting embodiment, the solid acid catalyst can be modified or functionalized with an acid comprising, consisting essentially of, or consisting of, benzoic acid; alternatively, formic acid; alternatively, acetic acid; alternatively, propionic acid; alternatively, butyric acid; alternatively, oxalic acid; alternatively, trifluoroacetic acid; alternatively, trichloroacetic acid; alternatively, sulfamic acid; alternatively, benzene sulfonic acid; alternatively, toluene sulfonic acid; alternatively, dodecylbenzene sulfonic acid; alternatively, naphthalene sulfonic acid; alternatively, dinonylnaphthalene disulfonic acid; or alternatively, methane sulfonic acid.

Non-Olefin Solvents

Illustrative non-olefin organic solvents which can be utilized in the processes disclosed herein, and/or in the internal olefin compositions, and/or olefin feeds disclosed herein, can include hydrocarbons, halogenated hydrocarbons, and combinations thereof. Hydrocarbon and halogenated hydrocarbon solvents can include, for example, aliphatic hydrocarbons, aromatic hydrocarbons, petroleum distillates, halogenated aliphatic hydrocarbons, halogenated aromatic hydrocarbons, or combinations thereof; alternatively, aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Generally, suitable solvents include solvents that do not react with the monomers, internal olefins, alpha olefins, etc., disclosed herein.

Aliphatic hydrocarbons which can be useful as an oligomerization solvent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified.

Non-limiting examples of suitable acyclic aliphatic hydrocarbon solvents that can be utilized singly or in any combination include pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons).

Non-limiting examples of suitable cyclic aliphatic hydrocarbon solvents include cyclohexane, methyl cyclohexane, and combinations thereof; alternatively cyclohexane; or alternatively, methylcyclohexane.

Aromatic hydrocarbons which can be useful as a solvent include $C_6$ to $C_{20}$ aromatic hydrocarbons; alternatively, $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

Halogenated aliphatic hydrocarbons which can be useful as a solvent include $C_2$ to $C_{15}$ halogenated aliphatic hydrocarbons; alternatively, $C_2$ to $C_{10}$ halogenated aliphatic hydrocarbons; or alternatively, $C_2$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized include chloroform, carbon tetrachloride, dichloroethane, trichloroethane, and combinations thereof; alternatively, chloroform, dichloroethane, trichloroethane, and combinations thereof; alternatively, methylene chloride; alternatively, chloroform; alternatively, carbon tetrachloride; alternatively, dichloroethane; or alternatively, trichloroethane.

Halogenated aromatic hydrocarbons which can be useful as a solvent include $C_6$ to $C_{20}$ halogenated aromatic hydrocarbons; alternatively, $C_6$ to $C_{15}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof; alternatively, chlorobenzene; or alternatively, dichlorobenzene.

Oligomer Products

Embodiments of the present invention also are directed to oligomer products produced from a monomer or internal olefin composition comprising internal olefins (for example, a monomer comprising $C_6$ to $C_{24}$ internal olefins, among others described herein). In some embodiments, the oligomer product can include a composition produced by any process(es) including an oligomerization step described herein. For instance, the present invention encompasses an oligomer product produced by a process comprising (i) contacting a monomer comprising internal olefins with a solid acid catalyst, and (ii) oligomerizing the monomer to form an oligomer product. The monomer can comprise, for example, at least 50 wt. % $C_6$ to $C_{24}$ internal olefins, at least 75 wt. % $C_6$ to $C_{24}$ internal olefins, or at least 90 wt. % $C_6$ to $C_{24}$ internal olefins (among monomers having other compositions described herein and internal olefin compositions described herein). Moreover, in a non-limiting embodiment, the oligomerization can be performed as described herein, for instance, contacting the monomer with an AMBERLYST® resin (e.g., AMBERLYST® 15 resin, or any solid acid catalyst or any resin disclosed herein) at a WHSV in a range from 0.05 to 5 (or at any other WHSV or WHSV range disclosed herein), and oligomerizing the monomer at a temperature in a range from 70° C. to 120° C. (or at any other temperature or temperature range disclosed herein). Still further, the monomer can comprise $C_8$ to $C_{24}$ internal olefins (or any other carbon number range of internal olefins disclosed herein), and/or less than 15 wt. % alpha olefins (or any other wt. % alpha olefins disclosed herein), and/or less than 50 ppm by weight of oxygen-containing and/or nitrogen-containing compounds (or any other ppm by weight of oxygen-containing and/or nitrogen-containing compounds described herein). Other embodiments of the oligomerization process(es) are readily apparent from the present disclosure.

It is contemplated that the oligomerization processes disclosed herein can have excellent selectivity to dimers, and thus, certain oligomer products disclosed herein can comprise at least 50 wt. % dimers. In some embodiments, the oligomer product can comprise at least 55 wt. % dimers, at least 60 wt. % dimers, at least 65 wt. % dimers, or at least 70 wt. % dimers. Moreover, the oligomer product can comprise at least 75 wt. % dimers, at least 80 wt. % dimers, or at least 85 wt. % dimers, in other embodiments. Thus, if the monomer or internal olefin composition is a $C_8$ internal olefin stream (or $C_{12}$ internal olefin stream), the oligomer product can have at least 50 wt. % $C_{16}$ olefins (or $C_{24}$ olefins), at least 60 wt. % $C_{16}$ olefins (or $C_{24}$ olefins), or at least 70 wt. % $C_{16}$ olefins (or $C_{24}$ olefins), and so forth.

In another embodiment, the ratio (mole or weight) of dimers to trimers and higher oligomers in the oligomer product can be greater than 2:1, greater than 3:1, or greater than 4:1. In another embodiment, the ratio (mole or weight) of dimers to non-dimer oligomer product in the oligomer product can be greater than 2:1, greater than 3:1, or greater than 4:1. In yet another embodiment, the ratio (mole or weight) of dimers to trimers and higher oligomers (or the ratio, mole or weight, of dimers to non-dimer oligomer product) in the oligomer product can be greater than 5:1, greater than 6:1, or greater than 8:1. Accordingly, mole or weight ratios of, for example, from 2:1 to 50:1, from 3:1 to 50:1, from 3:1 to 25:1, from 3:1 to 20:1, from 4:1 to 50:1, from 4:1 to 25:1, from 4:1 to 20:1, from 4:1 to 10:1, and the like, are encompassed herein.

Unexpectedly, the processes disclosed herein can be conducted for relatively long periods of time with low rates of catalyst deactivation (e.g., long catalyst lifetimes), and with relatively stable monomer (or internal olefin) conversion to dimers in the oligomer product (or dimer selectivity in the oligomer product). For example, a monomer conversion (or internal olefin conversion, or single pass monomer conversion, or single pass internal olefin conversion) to dimers (or dimer selectivity) in the oligomer product can be maintained substantially constant (i.e., within +/−25%) for a time period of at least 5 days, at least 7 days, at least 14 days, at least 21 days, or at least 30 days, and so forth. In some embodiments, the monomer conversion (or internal olefin conversion, or single pass monomer conversion, or single pass internal olefin conversion) to dimers can be maintained substantially constant for a maximum time period of 75 days, 60 days, 45 days, or 30 days. Generally, the monomer conversion (or internal olefin conversion, or single pass monomer conversion, or single pass internal olefin conversion) to dimers can be maintained substantially constant in a range from any minimum time period to any maximum time period disclosed herein. In some non-limiting embodiments, the monomer conversion (or internal olefin conversion, or single pass monomer conversion, or single pass internal olefin conversion) to dimers can be maintained substantially constant for a time period in a range from 5 to 60 days, from 7 to 60 days, from 10 to 60 days, from 5 to 45 days, from 7 to 45 days, from 10 to 45 days, from 5 to 30 days, from 7 to 30 days, or from 10 to 30 days. Other ranges of time periods are readily apparent from this disclosure. Moreover, these relatively stable conversions to dimers often can be maintained to within a range of +/−20%, to within a range of +/−15%, or to within a range of +/−10%, in certain embodiments, for these long periods of time. As an example, these long periods of time with stable single pass olefin conversion (or internal olefin conversion, or single pass olefin conversion, or single pass internal olefin conversion) to dimers can be achieved in a flow or continuous process, such as, for example, a single pass thru a reactor (e.g., a fixed bed reactor).

Embodiments of this invention are directed to processes for forming an oligomer product, such as by contacting a monomer comprising $C_6$ to $C_{24}$ internal olefins with a solid acid catalyst, and oligomerizing the monomer to form an oligomer product. In some embodiments, the oligomer product (alternatively, oligomers; alternatively, dimers; or alternatively, dimers and trimers) can be isolated, e.g., from the reactor effluent, residual non-oligomerized monomer, etc. Thus, any of the processes described herein optionally can further comprise a step of isolating the oligomer product (alternatively, oligomers; alternatively, dimers; or alternatively, dimers and trimers) and/or removing residual non-oligomerized monomer from the oligomer product.

In some embodiments, the oligomer product (alternatively, oligomers; alternatively, dimers; or alternatively, dimers and trimers) can be hydrogenated. Thus, any of the processes described herein optionally can further comprise a step of hydrogenating the oligomer product (alternatively, oligomers; alternatively, dimers; or alternatively, dimers and trimers). Suitable hydrogenation procedures and associated metal catalysts (e.g., platinum, rhenium, palladium, nickel, etc.) are well known to those of skill in the art.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

Gas chromatographic (GC) analyses were performed using a split injection method on an HP 5890 gas chromatograph with a flame ionization detector (FID). Initial oven temperature was 100° C. for 2 minutes and increased 8° C./min to 185° C., then 20° C./min to 290° C. for 6 minutes. The column was an HP-1 column, 12 m×0.2 mm×0.33 p.m. Data analysis was performed using Chemstation® software.

Sulfur analyses were performed in accordance with ASTM D5453-09, Standard Test Method for Determination of Total Sulfur in Light Hydrocarbons, Spark Ignition Engine Fuel, Diesel Engine Fuel, and Engine Oil by Ultraviolet Fluorescence.

Infrared (IR) results were based on monitoring the IR region between 1050-850 cm$^{-1}$, the absorbance band for C—H bending in olefins. Three different regions were integrated: 918-899 cm$^{-1}$ for alpha olefins, 974-954 cm$^{-1}$ for internal disubstituted olefins, and 899-874 cm$^{-1}$ for vinylidene and trisubstituted olefins. The baseline for integrating went from 1040-860 cm$^{-1}$. The reported mole % residual alpha olefin was determined via the equation: (100× alpha olefin area)/(sum of all three areas). If the resulting mole % of alpha olefin was less than 9%, the mole % of alpha olefin was re-calculated using the area from 990-930 cm$^{-1}$, instead of 974-954 cm$^{-1}$, for the internal disubstituted olefins.

Unless otherwise stated, continuous run experiments were conducted in a fixed bed reactor, which included a 2-inch ID stainless steel pipe with capacity for about 74 to 205 g of catalyst, and alundum inert packing material above and below the catalyst charge. A pump circulated liquid feed from a nitrogen-blanketed feed tank through the fixed bed at 20-70 psig. Product was collected in a separate tank, and samples were periodically removed for analytical analysis. Typical on-line time for the reactor ranged from 12 days to about 90 days.

Example 1

Oligomerization of 1-Octene with Fitrol Clay F-62

Fitrol clay F-62, sourced from BASF, was evaluated in Example 1 due to its large particle size being suitable for a fixed bed reactor process. 70 g of Fitrol clay F-62 were packed into the fixed bed reactor. Before initiating 1-octene feed, the Fitrol clay F-62 was dried at 275° C. in a stream of 2400 mL/min dry nitrogen for 18 hours. The catalyst activity of Fitrol clay F-62 was evaluated at a fixed WHSV of 0.6 for about 80 days, but at temperatures ranging from 140 to 180° C. The 1-octene feed was passed over a bed of 4 A mole sieves for removal of trace water and other oxygenates prior to entering the reactor. FIG. 1 illustrates the results of the oligomerization experiments with the F-62 catalyst, with the temperatures changed on the dates shown in FIG. 1.

Regenerations shown in FIG. 1 were performed as follows: dry nitrogen was passed over the catalyst at 2400 mL/min at 275° C. until no additional liquid was observed leaving the reactor. Then, 1.5 wt. % air was added into the nitrogen stream for 8 hr and continued heating at 275-300° C. Next, the air percentage was increased to 7 wt. % for 8 hr before switching back to 100% nitrogen and cooling the reactor.

It was concluded that Fitrol clay F-62 was not a suitable catalyst for a continuous oligomerization process, because the useful catalyst lifetimes were only about 4-5 days between regenerations. For example, at 160° C. and 0.6 WHSV, the initial conversion to $C_{16}$+ olefins of about 35 wt. % declined to less than 25 wt. % within 4-5 days.

Example 2

Oligomerization of 1-Octene with Fitrol Clay F-25

Fitrol clay F-25, sourced from BASF, was evaluated in Example 2 due to its large particle size being suitable for a fixed bed reactor process. The Fitrol clay F-25 acidic clay was evaluated in a manner similar to Example 1, and with similar results. During a 17-day study using Fitrol clay F-25, the conversion levels and deactivation rates were similar to those of Fitrol clay F-62. At 200° C. and 0.6 WHSV, maximum conversion was about 35 wt. %.

Example 3

Batch Oligomerization of Octenes with AMBERLYST® 15 Resin

Batch experiments were conducted by heating the olefin feed and the catalyst in small, capped bottles that were heated in a metal block on top of a magnetic stirrer. Typically, 2.5 g of dry AMBERLYST® 15 resin and 15 g of the selected octene composition were used. The mixture was stirred under nitrogen at ambient pressure and at temperatures in the 90-110° C. range, and samples were periodically removed by pipette and filtered prior to analytical analysis.

Figure 2:
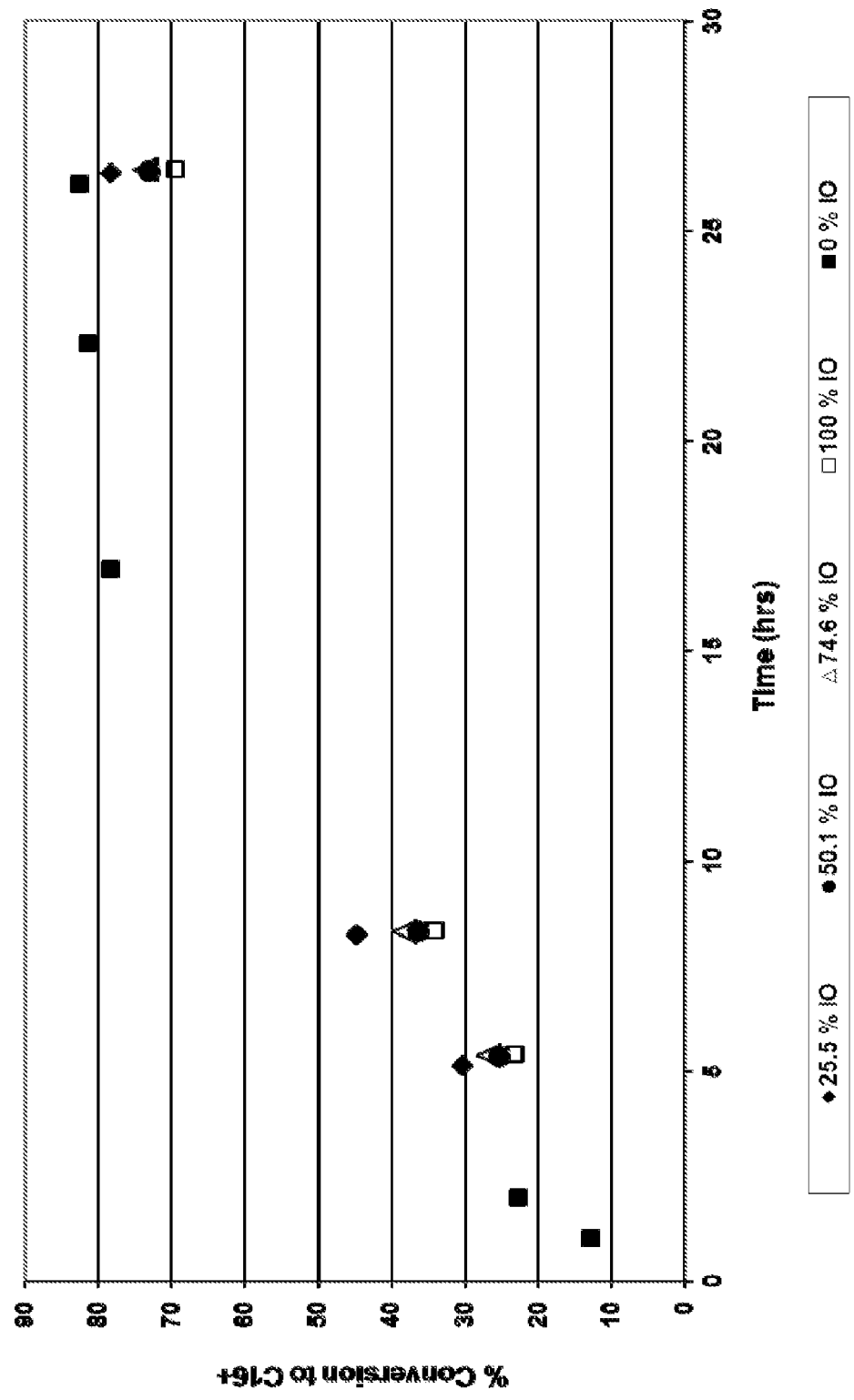
FIG. 2 presents a plot of the percentage conversion of various octene compositions to $C_{16}+$ oligomer product as a function of time using AMBERLYST® 15 resin in Example 3.

Using AMBERLYST® 15 resin, 70 wt. % conversion of octenes to $C_{16}$+ could be achieved, even if the starting olefins were almost 100% internal olefins (IO). FIG. 2 illustrates results for batch experiments using 14 wt. % AMBERLYST® 15 resin with various octene feed streams. As a feed olefin, 1-octene converted to $C_{16}$+ noticeably faster than did the internal octenes, but internal octenes still achieved 70 wt. % conversion during the experiment. The oligomer products obtained at about 5 hr of reaction in FIG. 2 contained about 85 wt. % $C_{16}$ olefins in the $C_{16}$+ fractions; by 24 hr of reaction, this level had dropped to about 75 wt. %. Generally, no significant levels of heavy (e.g., >$C_{48}$) olefins were detected in olefin products made using AMBERLYST® 15 resin. These experiments showed that good conversions to oligomer product could be achieved regardless of the quantity of alpha olefin present in the octene feedstock.

Examples 4-5

Oligomerization of 1-Octene with AMBERLYST® 15 Resin at 110° C. and at 100° C.

Figure 3:
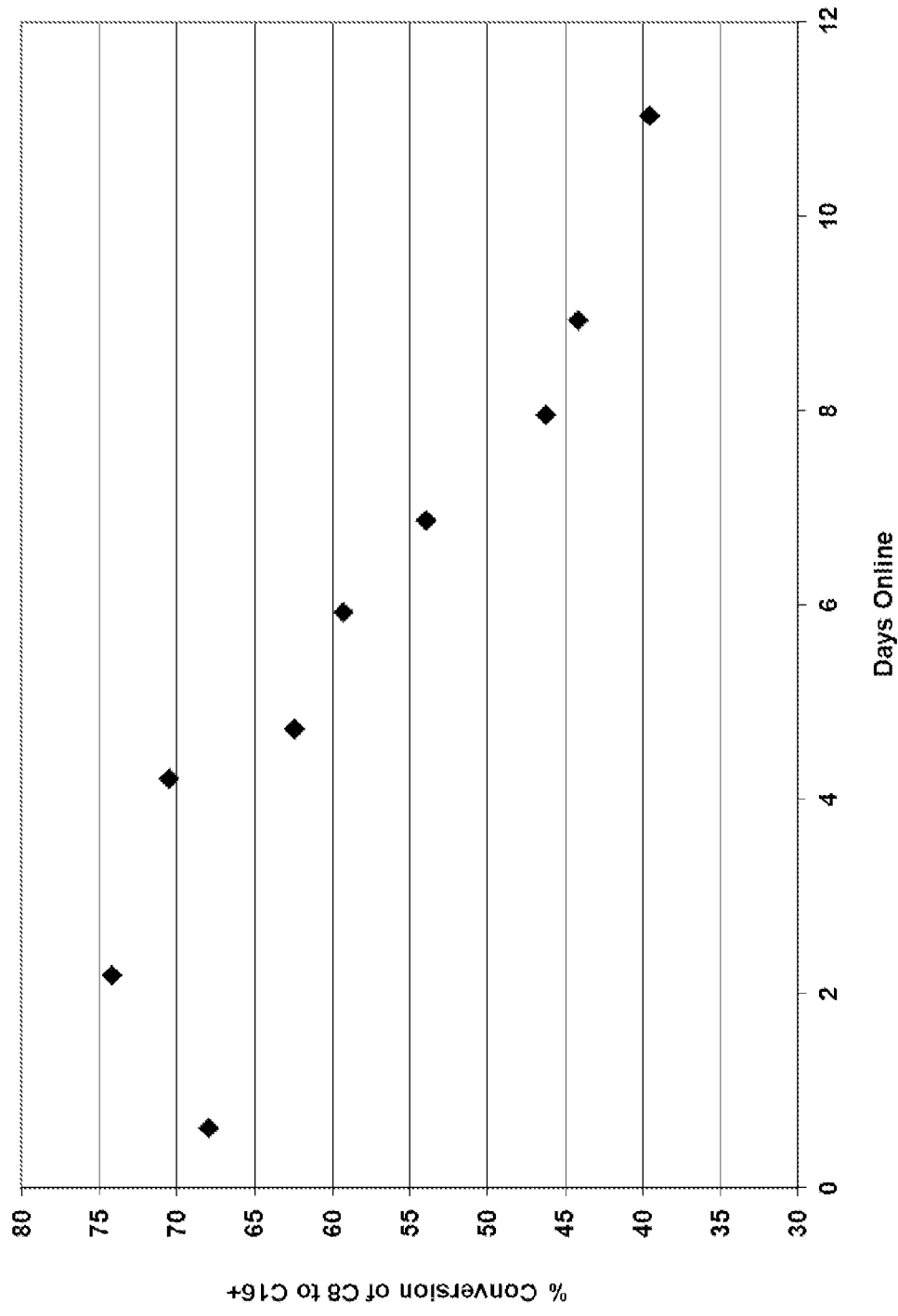
FIG. 3 presents a plot of the percentage conversion of 1-octene to $C_{16}+$ oligomer product as a function of time using AMBERLYST® 15 resin at 110° C. and 0.26 WHSV in Example 4.
Figure 4:
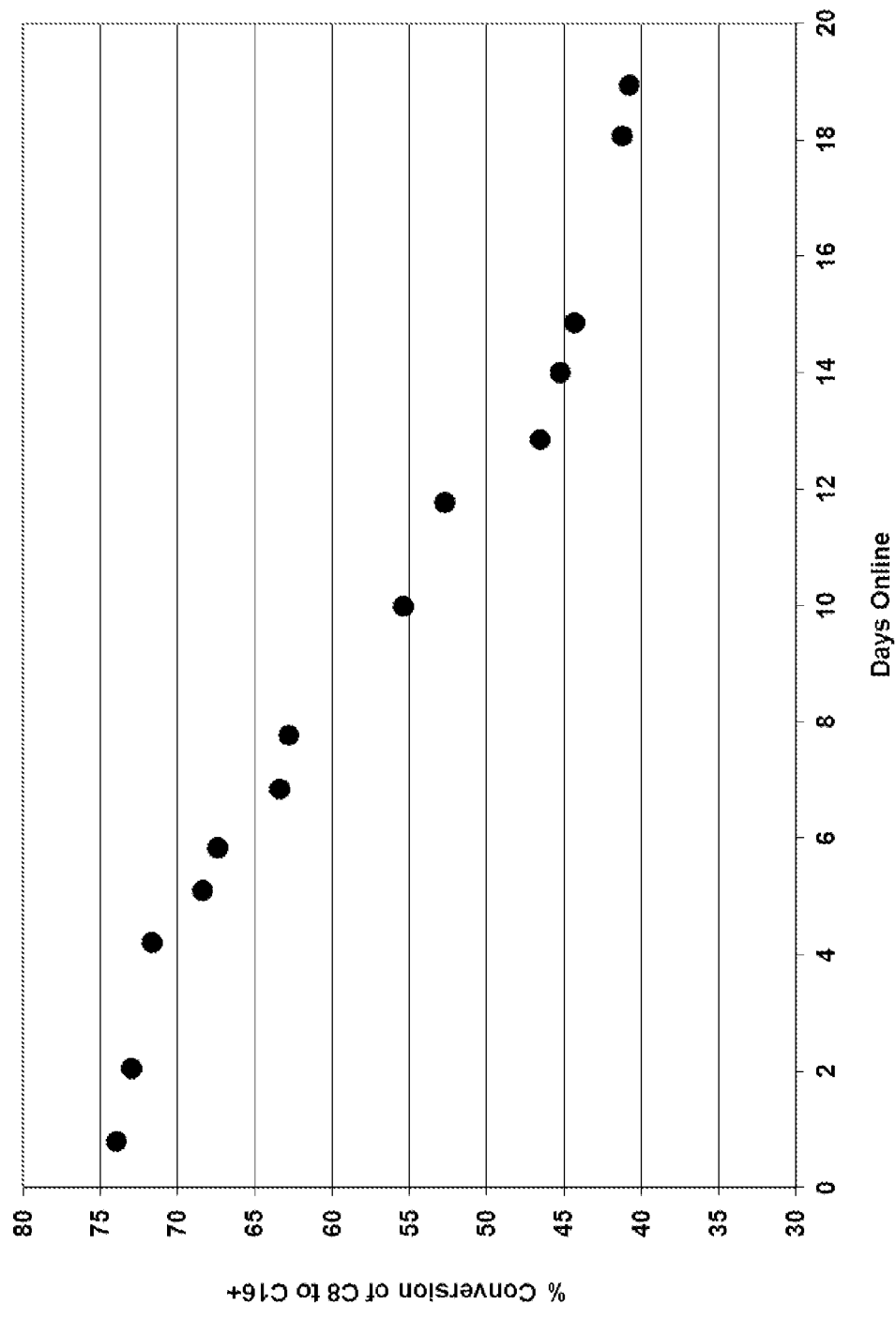
FIG. 4 presents a plot of the percentage conversion of 1-octene to $C_{16}+$ oligomer product as a function of time using AMBERLYST® 15 resin at 100° C. and 0.23 WHSV in Example 5.

AMBERLYST® 15 resin was evaluated in a fixed bed reactor oligomerization process in a manner similar to Example 1. Using 1-octene as the feed olefin, a steady decline in conversion to $C_{16}$+ was observed as the days on-line increased, as demonstrated in FIG. 3 (Example 4-110° C. and 0.26 WHSV) and FIG. 4 (Example 5-100° C. and 0.23 WHSV). The catalyst deactivation rate appeared to be higher at 110° C. than at 100° C.: At 110° C., conversion dropped from about 70 wt. % to 40 wt. % in 11 days, while at 100° C., conversion dropped from about 70 wt. % to 40 wt. % in about 20 days.

The reactor effluent of Example 4 was tested for sulfur to determine if sulfur was being extracted from the AMBERLYST® 15 resin (e.g., removing sulfonate groups) during oligomerization of the 1-octene feed. The effluent from day 4 in FIG. 3 contained 23.4 mg sulfur per liter (S/L). When the effluent obtained on days 6-7 was distilled, the $C_8$ distillate contained 2.3 mg S/L, while the $C_{16}$+ bottoms product contained 29 mg S/L.

Examples 6-7

Figure 5:
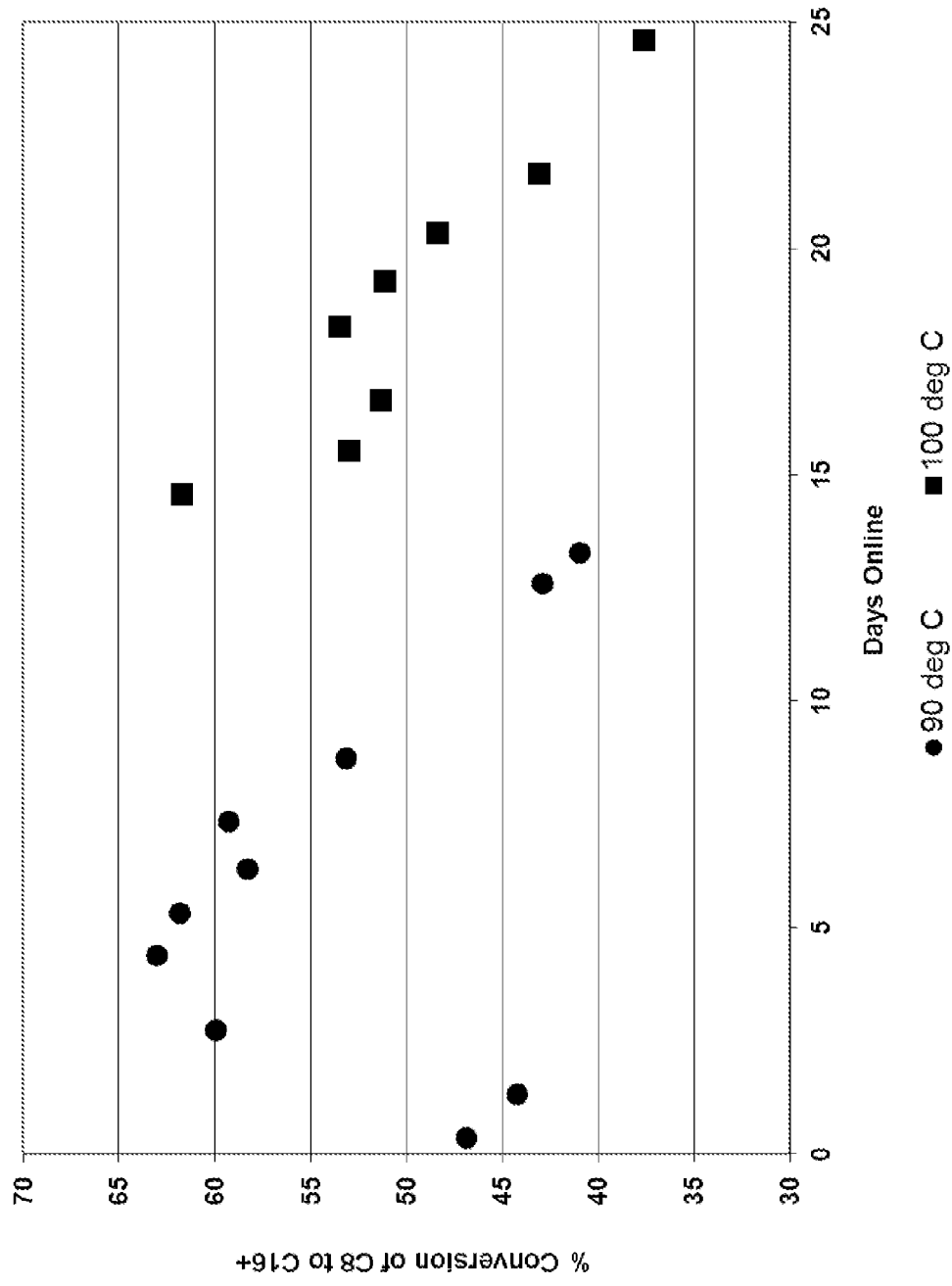
FIG. 5 presents a plot of the percentage conversion of 1-octene to $C_{16}+$ oligomer product as a function of time using AMBERLYST® 15 resin and small amounts of propionic acid in Examples 6-7.

Oligomerization of 1-Octene with AMBERLYST® 15 Resin at 100° C. and at 90° C. with Propionic Acid In an effort to extend the catalyst lifetime, AMBERLYST® 15 resin was evaluated with the addition of about 0.5-3 wt. % propionic acid to the 1-octene feed. As shown in FIG. 5, at both 100° C. (Example 6) and 90° C. (Example 7), a steady decline in conversion and catalyst activity over time was observed. The temperature was changed from 90° C. to 100° C. at about 14 days. For the 90° C. samples, the feed olefin contained 0.5 wt. % propionic acid, and for the 100° C. samples, the feed olefin contained 3 wt. % propionic acid. Catalyst deactivation rates appeared to be about the same for both sets of data. Because these feed streams contained propionic acid, the mole sieve drier bed was bypassed, and olefin was fed directly from the feed tank to the reactor.

Example 8

Oligomerization of Internal Octenes with AMBERLYST® 15 Resin at 90° C.

Figure 6:
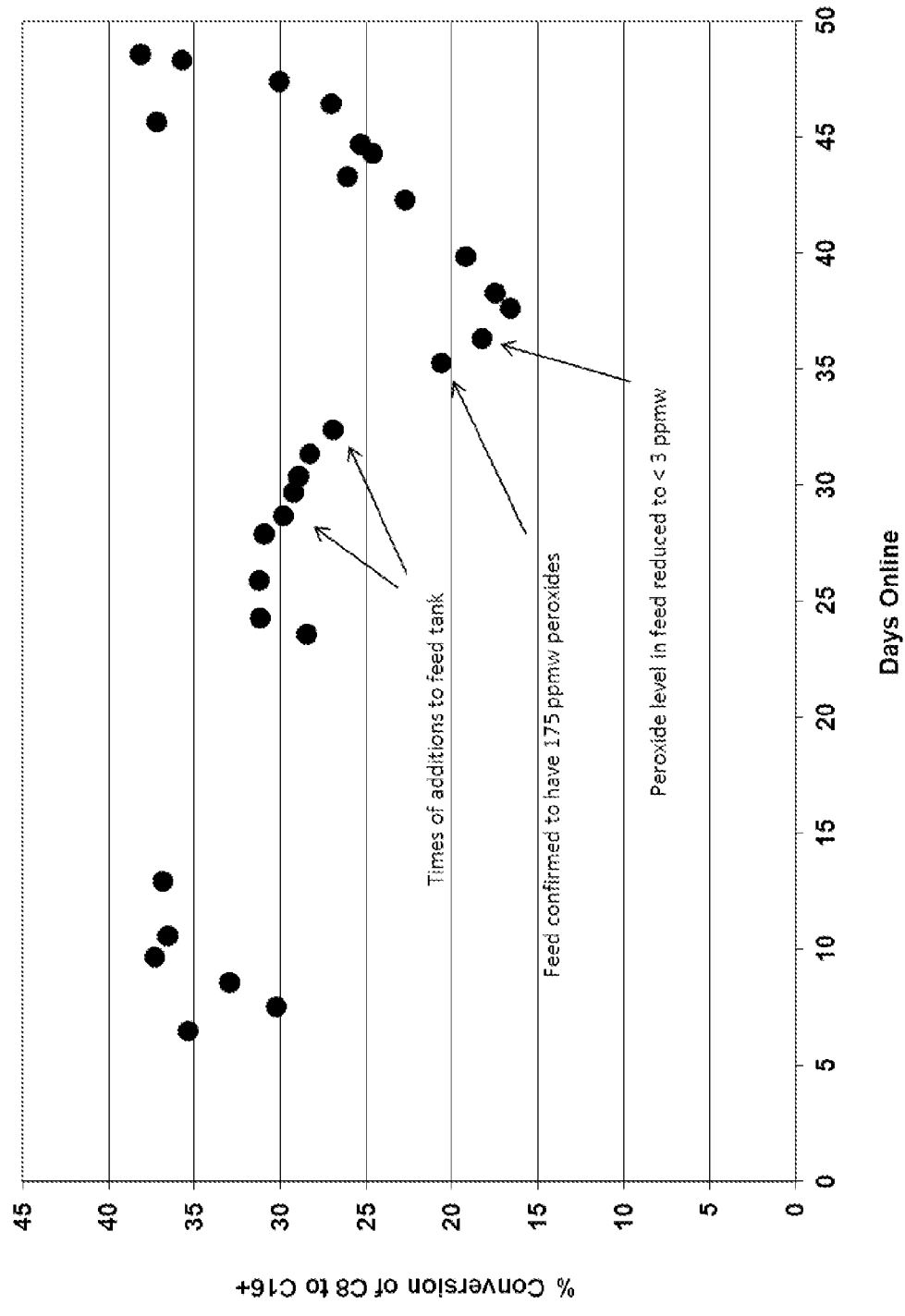
FIG. 6 presents a plot of the percentage conversion of $C_8$ internal olefins to $C_{16}+$ oligomer product as a function of time using AMBERLYST® 15 resin in Example 8.

AMBERLYST® 15 resin was evaluated in a fixed bed reactor oligomerization process in a manner similar to Example 1. Unexpectedly, using essentially 100% internal olefins, at 90° C. and 0.15-0.23 WHSV (average of 0.19), olefin conversion and catalyst activity remained relatively constant for almost 30 days (see FIG. 6). The use of internal olefins greatly extended the catalyst lifetime of the AMBERLYST® 15 resin as an oligomerization catalyst. Some of the scatter in the data was the result of a mechanical/pump issue. Nonetheless, the data in FIG. 6 demonstrated that olefin conversion around day 30 was about the same as the olefin conversion on days 5-10.

The olefin conversion dropped from about day 30 to day 35, during additions to the feed tank. It was determined that the olefin feed during this time period contained 175 ppm by weight peroxides, which began to poison and/or deactivate the catalyst and/or inhibit oligomerization. The peroxides were removed from the octene feed by filtering the internal octenes through alumina and/or 13× mole sieves. The mole sieve drier bed was bypassed during this work with the internal octenes feed.

The feed tank was replaced with internal octenes having <3 ppm by weight peroxides. There was an almost immediate increase in conversion, which continued steadily for several days, until the conversion eventually reached the same level observed at the start of the experiment. The negative impact of the peroxides on conversion appeared to be reversible.

Figure 7:
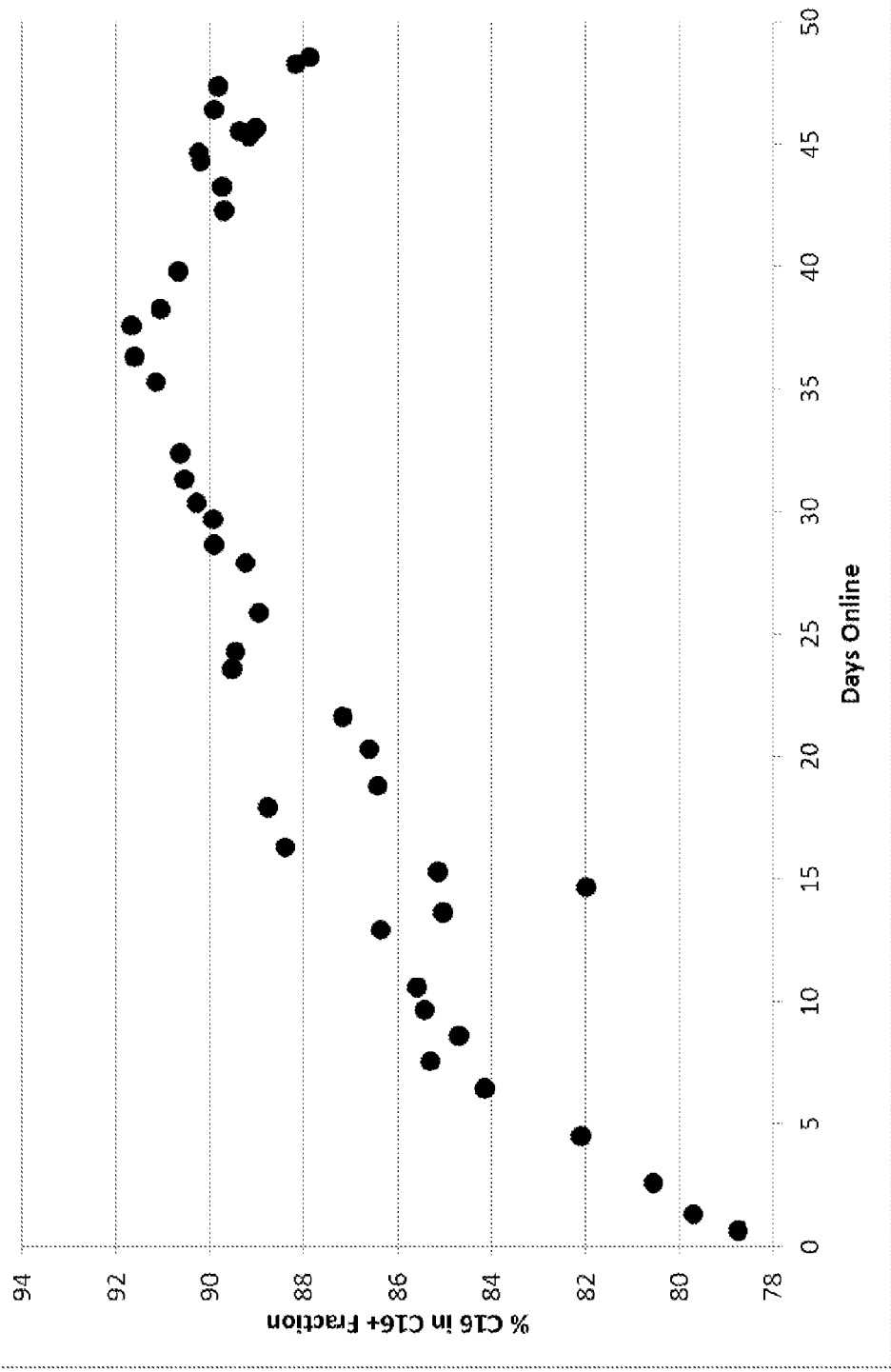
FIG. 7 presents a plot of the percentage of $C_{16}$ dimer in the $C_{16}+$ oligomer product as a function of time using AMBERLYST® 15 resin in Example 8.
Figure 8:
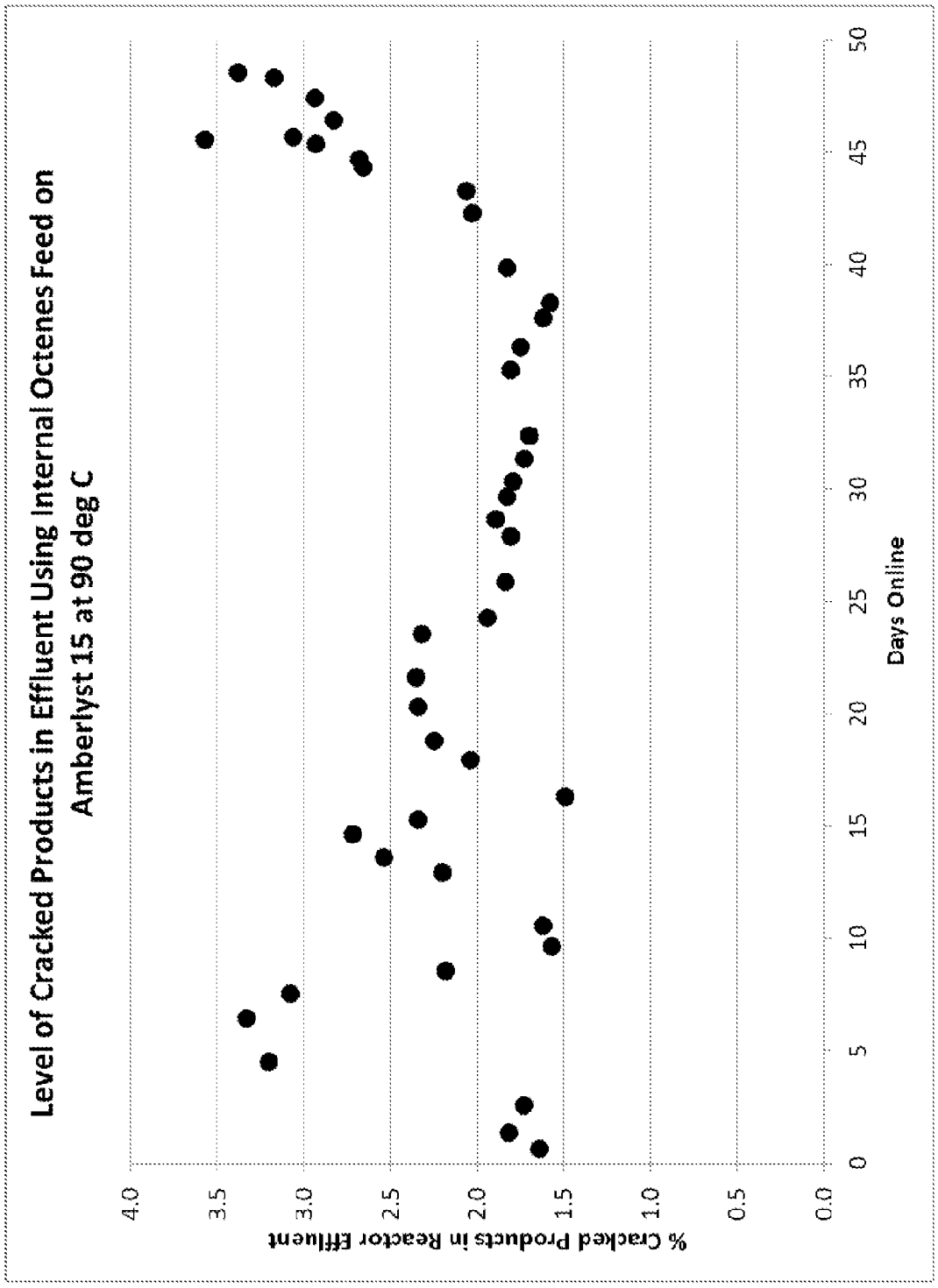
FIG. 8 presents a plot of the percentage of $C_9$ to $C_{12}$ cracked products in the reactor effluent as a function of time using AMBERLYST® 15 resin in Example 8.

The amount of dimer ($C_{16}$) in the oligomer product produced from internal octenes is illustrated in FIG. 7. The composition of the oligomer product ($C_{16}$+ only) reached a nearly steady state after about two weeks of continuous reactor operation. On day 5, about 82 wt. % of the oligomer product was $C_{16}$ olefins, and on day 50, this value was about 88 wt. %. During the time frame of high peroxide feed and declining catalyst activity, $C_{16}$ content in the oligomer product reached as high as about 92 wt. %, before dropping back to 88 wt. % as activity returned with the introduction of lower peroxide feed olefins. The level of cracked products in the $C_9$-$C_{12}$ range did not change appreciably over the course of the experiment, as illustrated in FIG. 8.

Figure 9:
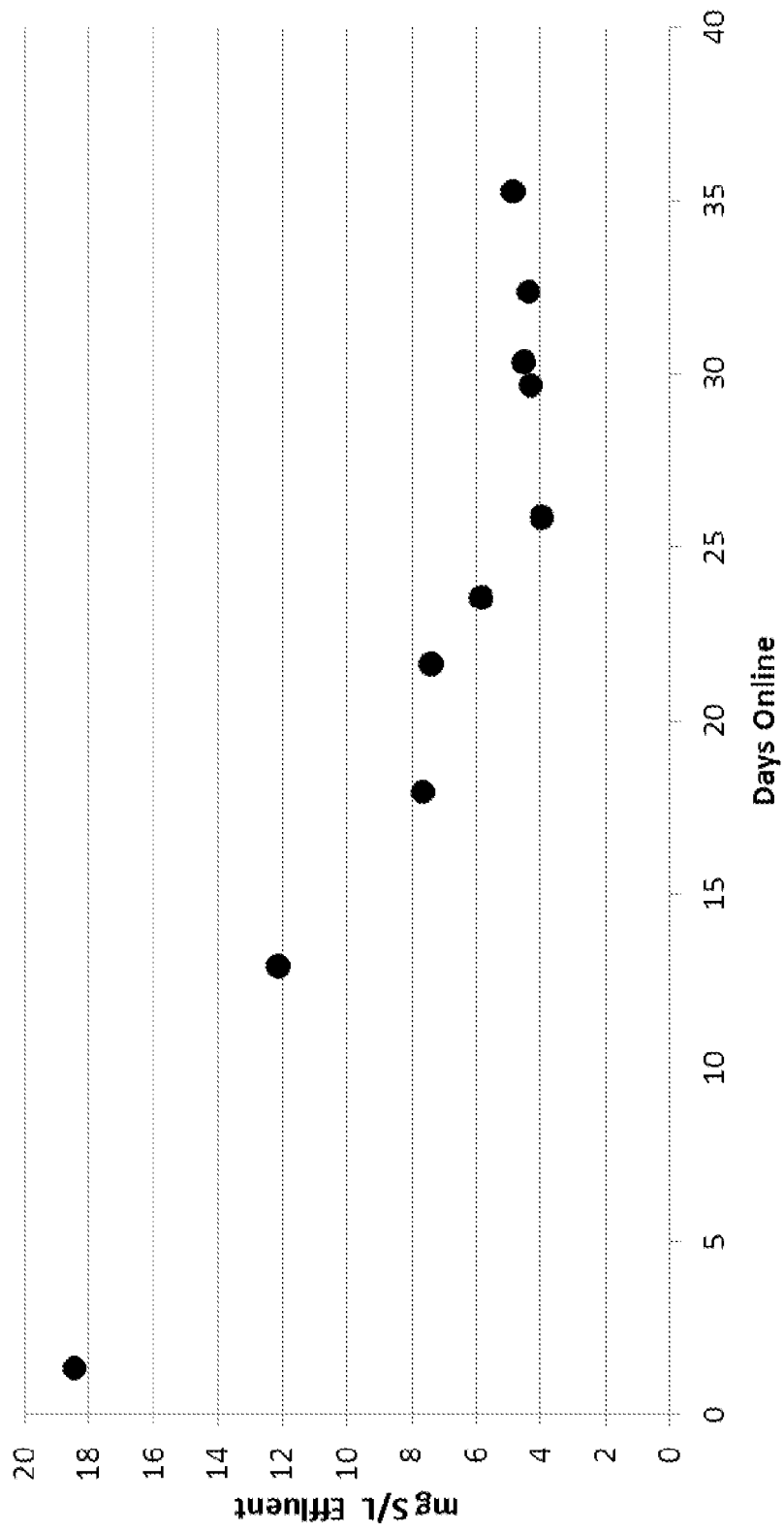
FIG. 9 presents a plot of the percentage of sulfur in the reactor effluent as a function of time using AMBERLYST® 15 resin in Example 8.

The reactor effluent was tested for sulfur to determine if sulfur was being extracted from the AMBERLYST® 15 resin (e.g., removing sulfonate groups) during oligomerization of the internal octenes. FIG. 9 summarizes these results at a reactor temperature of 90° C. and WHSV of 0.2. With an initial catalyst charge of 205 g, the sulfur content in the effluent declined from about 20 mg of sulfur per liter (S/L) at the start of the run to about 4 mg S/L 25 days later. Sulfur content in the effluent stabilized at about 4-5 mg S/L out to 35 days online, at which time the sulfur testing was discontinued. Olefin conversion was holding steady during this time, so the sulfur removal did not appear to significantly impact catalyst activity.

Table I summarizes physical properties of the oligomer product ($C_{16}$+ only) produced in Example 8 at a time period where the selectivity to the $C_{16}$ dimer was 88 wt. %.

TABLE I

Physical Properties of Typical $C_{16}$+ Oligomer Product Using AMBERLYST ® 15 catalyst resin

| | |
|---|---|
| Viscosity @ 0° C. (cSt) | 11.13 |
| Viscosity @ 25° C. (cSt) | 4.72 |
| Viscosity @ 40° C. (cSt) | 3.27 |
| Viscosity @ 100° C. (cSt) | 1.22 |
| Flash point (° C.) | 132 |
| Fire point (° C.) | 134 |
| Pour Point (° C.) | <-90 |
| Specific Gravity (at 15.5° C.) | 0.7956 |

Example 9

Oligomerization of $C_{16}$ Internal Olefins, or of a Composition Containing a Mixture of $C_{16}$ and $C_{18}$ Internal Olefins, with AMBERLYST® 15 Resin at 90° C.

Figure 10:
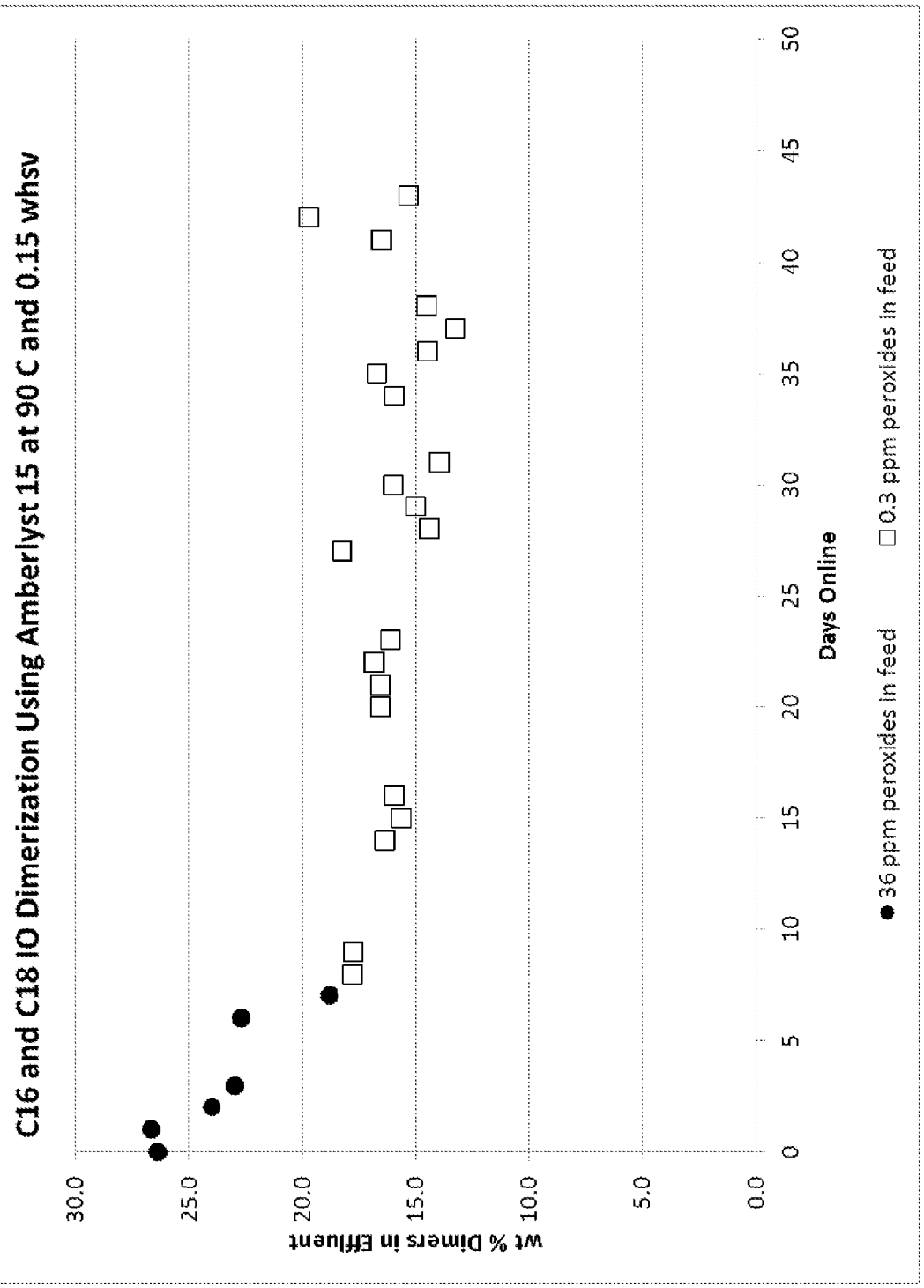
FIG. 10 presents a plot of the percentage of dimer from $C_{16}$ internal olefins, or from a mixture of $C_{16}$ and $C_{18}$ internal olefins, in the reactor effluent as a function of time using AMBERLYST® 15 resin in Example 9.

AMBERLYST® 15 resin was evaluated in a fixed bed reactor oligomerization process in a manner similar to Example 1, except that a ¾-inch ID tubular reactor was employed. Using 63 g of AMBERLYST® 15 resin at 90° C. and 0.15 WHSV, the dimer yield for $C_{16}$ (or for mixed $C_{16}$+$C_{18}$) internal olefins was tested for 45 days. During the 45-day test, the composition of the olefin feed was either $C_{16}$ internal olefins or a mixture of $C_{16}$ and $C_{18}$ internal olefins. Surprisingly, as shown in FIG. 10, the dimer yield was relatively constant for 45 days. For about the first week, the internal olefin feed stream contained about 36 ppm by weight peroxides, while afterwards, the internal olefin feed contained only about 0.3 ppm by weight peroxides.

I claim:
1. A process comprising:
   (i) contacting a monomer comprising at least 50 wt. % linear internal olefins with a solid acid catalyst comprising a sulfonated styrene-divinylbenzene copolymer acid resin; and
   (ii) oligomerizing the monomer to form an oligomer product.
2. The process of claim 1, wherein the monomer comprises at least 75 wt. % $C_8$ to $C_{24}$ linear internal olefins and less than 15 wt. % $C_8$ to $C_{24}$ alpha olefins.
3. The process of claim 1, wherein the monomer comprises at least 95 wt. % $C_8$ to $C_{20}$ linear internal olefins and less than 5 wt. % $C_8$ to $C_{20}$ alpha olefins.
4. The process of claim 1, wherein the monomer comprises $C_8$ linear internal olefins, $C_{10}$ linear internal olefins, $C_{12}$ linear internal olefins, $C_{14}$ linear internal olefins, $C_{16}$ linear internal olefins, or any combination thereof.
5. The process of claim 1, wherein:
   a) the monomer is substantially free of oxygen-containing compounds;
   b) the monomer is substantially free of nitrogen-containing compounds; or
   c) the monomer is substantially free of oxygen-containing compounds and nitrogen-containing compounds.
6. The process of claim 1, wherein:
   a) a single pass conversion of the monomer to the oligomer product is at least 10 wt. %;
   b) a single pass conversion of the monomer to the oligomer product is maintained substantially constant for a time period of at least 5 days; or
   c) the single pass conversion of the monomer to the oligomer product is at least 10 wt. % and the single pass conversion of the monomer to the oligomer product is maintained substantially constant for a time period of at least 5 days.

7. The process of claim 1, wherein:
a) a single pass conversion of the monomer to the oligomer product is at least 15 wt. %;
b) a single pass conversion of the monomer to the oligomer product is maintained substantially constant for a time period of at least 14 days; or
c) the single pass conversion of the monomer to the oligomer product is at least 15 wt. % and the single pass conversion of the monomer to the oligomer product is maintained substantially constant for a time period of at least 14 days.

8. The process of claim 1, wherein:
a) the oligomer product comprises at least 50 wt. % dimers;
b) a weight ratio of dimers to trimers and higher oligomers in the oligomer product is greater than 4:1; or
c) the oligomer product comprises at least 50 wt. % dimers and the weight ratio of dimers to trimers and higher oligomers in the oligomer product is greater than 4:1.

9. The process of claim 1, wherein:
a) the monomer and the solid acid catalyst are contacted at a WHSV in a range from 0.05 to 5;
b) the oligomerizing step is conducted at a temperature below a maximum operating temperature of the solid acid catalyst; or
c) the monomer and the solid acid catalyst are contacted at a WHSV in a range from 0.05 to 5 and the oligomerizing step is conducted at a temperature below a maximum operating temperature of the solid acid catalyst.

10. The process of claim 1, further comprising a step of isomerizing an olefin feed to form the monomer.

11. The process of claim 1, further comprising a step of isolating the oligomer product.

12. A process comprising:
(a) isomerizing an olefin feed comprising linear olefins to produce a linear internal olefin composition comprising linear internal olefins;
(b) contacting the linear internal olefin composition comprising linear internal olefins with a solid acid catalyst comprising a sulfonated styrene-divinylbenzene copolymer acid resin; and
(c) oligomerizing the linear internal olefin composition comprising linear internal olefins to form an oligomer product;
wherein the linear olefins of the olefin feed comprise at least 50 wt. % $C_6$ to $C_{24}$ normal alpha olefins, and linear olefins of the linear internal olefin composition comprise at least 50 wt. % $C_6$ to $C_{24}$ hydrocarbon linear internal olefins.

13. The process of claim 12, wherein:
the linear olefins of the olefin feed comprise at least 75 wt. % $C_6$ to $C_{24}$ normal alpha olefins; and
the linear olefins of the linear internal olefin composition comprise less than 10 wt. % $C_6$ to $C_{24}$ normal alpha olefins.

14. The process of claim 12, wherein:
the linear olefins of the olefin feed comprise at least 90 wt. % $C_6$ to $C_{24}$ normal alpha olefins; and
the linear olefins of the linear internal olefin composition comprise less than 2 wt. % $C_6$ to $C_{24}$ normal alpha olefins.

15. The process of claim 12, wherein:
a single pass conversion of the linear internal olefin composition to the oligomer product is at least 10 wt. % and the single pass conversion of the linear internal olefin composition to the oligomer product is maintained substantially constant for a time period in a range from 5 to 60 days; or
a single pass conversion of the linear internal olefin composition to the oligomer product is at least 15 wt. % and the single pass conversion of the linear internal olefin composition to the oligomer product is maintained substantially constant for a time period in a range from 10 to 45 days.

16. A process comprising:
(i) contacting a monomer comprising at least 50 wt. % $C_8$ to $C_{12}$ linear internal olefins with a solid acid catalyst comprising a sulfonated styrene-divinylbenzene copolymer acid resin; and
(ii) oligomerizing the monomer to form an oligomer product.

17. The process of claim 16, wherein the monomer comprises at least 75 wt. % $C_8$ to $C_{12}$ linear internal olefins and less than 15 wt. % $C_8$ to $C_{12}$ alpha olefins.

18. The process of claim 17, wherein:
a single pass conversion of the monomer to the oligomer product is maintained substantially constant for a time period in a range from 5 to 60 days; or
a single pass conversion of the monomer to the oligomer product is at least 10 wt. % and the single pass conversion of the monomer to the oligomer product is maintained substantially constant for a time period in a range from 5 to 60 days.

19. The process of claim 17, wherein:
a single pass conversion of the monomer to the oligomer product is maintained substantially constant for a time period in a range from 10 to 45 days; or
a single pass conversion of the monomer to the oligomer product is at least 15 wt. % and the single pass conversion of the monomer to the oligomer product is maintained substantially constant for a time period in a range from 10 to 45 days.

20. The process of claim 17, wherein the monomer comprises at least 95 wt. % $C_8$ to $C_{12}$ linear internal olefins and less than 5 wt. % $C_8$ to $C_{12}$ alpha olefins.

21. The process of claim 17, wherein the oligomer product comprises at least 50 wt. % dimers, and a weight ratio of dimers to trimers and higher oligomers in the oligomer product is greater than 4:1.

22. A process comprising:
(a) isomerizing an olefin feed comprising linear olefins to produce a linear internal olefin composition comprising linear internal olefins;
(b) contacting the linear internal olefin composition comprising linear internal olefins with a solid acid catalyst comprising a sulfonated styrene-divinylbenzene copolymer acid resin; and
(c) oligomerizing the linear internal olefin composition comprising linear internal olefins to form an oligomer product;
wherein the linear olefins of the olefin feed comprise at least 50 wt. % $C_8$ to $C_{12}$ normal alpha olefins, and linear olefins of the linear internal olefin composition comprise at least 50 wt. % $C_8$ to $C_{12}$ hydrocarbon linear internal olefins.

23. The process of claim 22, wherein:
the linear internal olefin composition comprises at least 75 wt. % $C_8$ to $C_{12}$ hydrocarbon linear internal olefins and less than 15 wt. % $C_8$ to $C_{12}$ alpha olefins.

24. The process of claim 22, wherein:
a single pass conversion of the linear internal olefin composition to the oligomer product is at least 10 wt. % and the single pass conversion of the linear internal olefin composition to the oligomer product is maintained substantially constant for a time period in a range from 5 to 60 days.

* * * * *